US009862783B2

(12) United States Patent
Tanna et al.

(10) Patent No.: US 9,862,783 B2
(45) Date of Patent: Jan. 9, 2018

(54) IMINE COMPOUND, NOVEL CATALYST FOR OLEFIN POLYMERIZATION, AND PROCESS FOR PRODUCING OLEFIN POLYMER

(71) Applicants: JAPAN POLYPROPYLENE CORPORATION, Tokyo (JP); JAPAN POLYETHYLENE CORPORATION, Tokyo (JP)

(72) Inventors: Akio Tanna, Mie (JP); Naomasa Sato, Kanagawa (JP); Yohei Konishi, Kanagawa (JP); Yasuo Oishi, Kanagawa (JP)

(73) Assignees: JAPAN POLYPROPYLENE CORPORATION, Tokyo (JP); JAPAN POLYETHYLENE CORPORATION, Tokyo (JP)

( * ) Notice: Subject to any disclaimer, the term of this patent is extended or adjusted under 35 U.S.C. 154(b) by 0 days.

(21) Appl. No.: 15/024,591

(22) PCT Filed: Sep. 26, 2014

(86) PCT No.: PCT/JP2014/075656
§ 371 (c)(1),
(2) Date: Mar. 24, 2016

(87) PCT Pub. No.: WO2015/046438
PCT Pub. Date: Apr. 2, 2015

(65) Prior Publication Data
US 2016/0237184 A1 Aug. 18, 2016

(30) Foreign Application Priority Data
Sep. 27, 2013 (JP) ................................. 2013-201474

(51) Int. Cl.
C08F 10/06 (2006.01)
C07F 15/04 (2006.01)
C07F 9/50 (2006.01)
C07F 15/00 (2006.01)
C08F 210/06 (2006.01)

(52) U.S. Cl.
CPC ............ *C08F 10/06* (2013.01); *C07F 9/5022* (2013.01); *C07F 15/0066* (2013.01); *C07F 15/0093* (2013.01); *C07F 15/045* (2013.01); *C08F 210/06* (2013.01)

(58) Field of Classification Search
None
See application file for complete search history.

(56) References Cited

U.S. PATENT DOCUMENTS 3,836,569 A  9/1974 Wommack
3,987,023 A  10/1976 McCrae et al.
4,045,470 A  8/1977 Knapp, Jr.
4,241,079 A  12/1980 Kilbourn et al.
6,103,658 A  8/2000 MacKenzie et al.
7,129,292 B1 10/2006 Kristen et al.

FOREIGN PATENT DOCUMENTS

| JP | S50-059419 A | 5/1975 |
|----|--------------|--------|
| JP | 4-89869 A | 3/1992 |
| JP | 04-089869 A | 3/1992 |
| JP | 4-239061 A | 8/1992 |
| JP | 04-239061 A | 8/1992 |
| JP | 11-158213 A | 6/1999 |
| JP | H11-15213 A | 6/1999 |
| JP | 2001-519841 A | 10/2001 |
| JP | 2002-541275 A | 12/2002 |
| JP | 2003-517062 A | 5/2003 |
| JP | 2014-039515 A | 3/2014 |
| WO | 00/59956 A | 10/2000 |
| WO | 01/44325 A1 | 6/2001 |

OTHER PUBLICATIONS

Jeewoth et al., "Synthesis, characterization and antibacterial properties of Schiff bases and Schiff base metal complexes derived from 2,3-diamino-pyridine," Transition Met. Chem., 24, 45-448 (1999).*
Dian Chen et al., "New Synthetic Cobalt Schiff Base Complexes as Oxygen Carriers", Inorg. Chem., vol. 28, No. 13, 1989, pp. 2647-2652.
Ramunas J. Motekaitis et al., "Potentiometric Determination of the Stabilities of Cobalt (II) Complexes of Polyamine Schiff Bases and Their Dioxygen Adducts", Inorg. Chem., vol. 27, No. 15, 1988, pp. 2718-2724.
Jorg Wagner et al., "Novel trigonal prismatic iron complexes of expanded hexadentate Jager type ligands: synthesis and X-ray analysis", Inorganica Chimica Acta, 358, 2004, pp. 808-813.
Jorg Wagner et al., "Expanded hexadentate ligands of Jager Type: synthesis and X-ray analysis", Inorganic Chemistry Communications, 5, 2002, pp. 78-81.
Tatsuhito Kino et al., "Pd-catalysed coupling of arylamines and 2-bromo-3,3,3-trifluoropropene", Journal of Molecular Catalysis A: Chemical, 282, 2007, pp. 34-51.
Chinese Office Action issued with respect to Application No. 201480053047.2, dated Nov. 21, 2016.
Extended European Search Report issued with respect to Application No. 14849192.1, dated Oct. 5, 2016.
Kino et al., "Pd-catalyzed coupling of arylamines and 2-bromo-3,3,3-triflouropropene", Journal of Molecular Catalysis A: Chemical, vol. 282, 2008, pp. 34-51.

(Continued)

*Primary Examiner* — Catherine S Branch
(74) *Attorney, Agent, or Firm* — Greenblum & Bernstein, P.L.C.

(57) ABSTRACT

A compound represented by the following general formula (1):

$$\begin{array}{c} R^2 \diagdown \diagup R^1 \\ \| \\ R^3 \diagup \diagdown X \\ | \\ R^4 \diagdown Y \\ \diagup \diagdown \\ R^5 \quad R^6 \end{array} \quad (1)$$

11 Claims, No Drawings

(56) References Cited

OTHER PUBLICATIONS

Motekaitis et al., "Potentiometric Determination of the Stabilities of Cobalt(II) Complexes of Polyamine Schiff Bases and Their Dioxygen Adducts", Inorg. Chem., vol. 27, 1988, pp. 2718-2724.
Shi et al., "Palladium(II) Complexes Containing P—N—O Donors. Preparation and Reactivity", Journal of the Chinese Chemical Society, vol. 50, 2003, pp. 89-94.
Beuken et al., "Oligomerisation of ethene by new palladium iminophosphine catalysts", Chem. Commun., 1998, pp. 223.
Wagner et al., "Novel trigonal prismatic iron complexes of expanded hexadentate Jager type ligands: synthesis and X-ray analysis", Inorganica Chimica Acta, vol. 358, 2005, pp. 808-813.
Chen et al., "New Synthetic Cobalt Schiff Base Complexes as Oxygen Carriers", Inorg. Chem., vol. 28, 1989, pp. 2647-2652.
Wang et al., "Neutral Nickel(II)-Based Catalysts for Ethylene Polymerization", Organometallics, vol. 17, 1998, pp. 3149-3151.
Johnson et al., "New Pd(II)- and Ni(II)-Based Catalysts for Polymerization of Ethylene and a-Olefins", J. Am. Chem. Soc., vol. 117, 1995, pp. 6414-6415.
Wagner et al., "Expanded hexadentate ligands of Jager type: synthesis and X-ray analysis", Inorganic Chemistry Communications, vol. 5, 2002, pp. 78-81.
International Search Report issued with respect to application No. PCT/JP2014/075656, dated Jan. 6, 2015.
International Preliminary Report on Patentability issued with respect to application No. PCT/JP2014/075656, dated Mar. 29, 2016.
Notification of Reasons for Refusal issued with respect to Application No. 2013-201474, dated Feb. 21, 2017.
European Office Action issued with respect to Application No. 14849192.1, dated Mar. 31, 2017.
Chinese Office Action issued with respect to Chinese patent Application No. 20140053047.2 dated Jul. 12, 2017.

* cited by examiner

IMINE COMPOUND, NOVEL CATALYST FOR OLEFIN POLYMERIZATION, AND PROCESS FOR PRODUCING OLEFIN POLYMER

TECHNICAL FIELD

The present invention relates to a novel imine compound, a metal complex obtained using the compound, an α-olefin polymerization catalyst based on these, and a process for producing an α-olefin-based polymer.

BACKGROUND ART

Polyethylene resins and polypropylene resins are widely used as major polymers among polyolefin resins in various industrial fields. Because these resins are exceedingly important industrial materials, the various performances thereof are always required to be further improved.

The catalysts for use in producing such polyolefin resins are limited to heterogeneous-system solid catalysts such as Ziegler-Natta catalysts and Phillips catalysts and homogeneous-system catalysts employing a solvent-soluble metal complex, such as metallocene catalysts.

Under the influence of the rapid advances of metallocene catalysts, complexes different from the metallocene complexes are being developed enthusiastically in recent years, such complexes being called post-metallocene complexes. Among such post-metallocene complexes, complexes of late transition metals are attracting attention, and a large number of late transition metal complexes mainly having a bidentate ligand have been reported.

Representative late transition metal complexes having a bidentate ligand include the diimine complex proposed by Brookhart et al. (non-patent document 1) and the salicylaldimine complex proposed by Grubbs et al. (non-patent document 2). These discoveries were followed by reports on late transition metal complexes having various bidentate ligands such as an unsymmetric iminopyridine, pyridinecarboxamide, and iminophophine, and on the usefulness thereof as ethylene polymerization catalysts. Of these complexes, the late transition metal complexes of the iminophosphine type are complexes on which many investigations have been made from both the industrial and the scientific standpoints because these complexes have a nitrogen atom and a phosphorus atom which differ in donor characteristics.

However, in patent documents (patent documents 1, 2, 3, and 4) and non-patent documents (non-patent documents 3 and 4) which relate to late metal complexes having an iminophosphine bidentate ligand, there are the only examples of polymerization for ethylene oligomers or polymers. No report is given therein on polymerization of an α-olefin other than ethylene.

PRIOR-ART DOCUMENTS

Patent Documents

Patent Document 1: JP-A-11-158213
Patent Document 2: JP-T-2001-519841 (The term "JP-T" as used herein means a published Japanese translation of a PCT patent application.)
Patent Document 3: JP-T-2002-541275
Patent Document 4: JP-T-2003-517062

Non-Patent Documents

Non-Patent Document 1: Johnson L. K., Killian C. M., Brookhart M., *J. Am. Chem. Soc.*, 1995, 117, 6414.
Non-Patent Document 2: Chunming Wang, Stefan Friedrich, Todd R. Younkin, Robert T. Li, Robert H. Grubbs, Donald A. Bansleben, and Michael W. Day, *Organometallics*, 1998, 17, 3149.
Non-Patent Document 3: Ping-Yung Shi, Yi-Hong Liu, Shie-Ming Peng and Shiuh-Tzung Liu, *Journal of the Chinese Chemical Society*, 2003, 50, 89.
Non-Patent Document 4: Esther K. van den Beuken, Wilberth J. J. Smeets, Anthony L. Spek and Ben L. Feringa. *Chem. Commun.*, 1998, 223.

SUMMARY OF THE INVENTION

Problem that the Invention is to Solve

As will be demonstrated herein by the Comparative Example, the conventionally known iminophosphine late metal complexes are effective only for the oligomerization of α-olefins, in particular, propylene. Further improvements have been desired from the standpoint of using these complexes as catalysts for α-olefin polymerization.

An object of the invention, in view of the problem of prior-art techniques concerning the late transition metal complexes having an iminophosphine bidentate ligand, is to provide a ligand compound capable of forming a metal complex which can produce a high-molecular-weight polymer of α-olefin and which further renders copolymerization of an α-olefin with an acrylic acid ester possible, and to further provide a polymerization catalyst for polyolefins that includes the ligand compound and a process for polymerizing an α-olefin using the catalyst.

Means for Solving the Problem

The present inventors diligently made investigations in order to overcome the problem. As a result, the inventors have discovered that when a transition metal complex including a bidentate ligand having a specific structure wherein at least one of the two substituents, $R^5$ and $R^6$, on the phosphorus or nitrogen atom (indicated by Y in the invention) is a hydrocarbon group including two or more heteroatom-containing groups is used as a catalyst component to conduct polymerization of an α-olefin, then a polymer having an exceedingly high molecular weight is obtained. In addition, it has been discovered that use of this transition metal complex renders copolymerization of an α-olefin with acrylic acid esters possible. The present invention has been thus achieved.

The imine compound which constitutes a base of the present invention has a peculiar structure and is hence novel as a bidentate ligand. This compound is characterized by constituting chemical, steric, and electronic environments for a complex structure, and these environments bring about a catalytic function which renders the desirable polymerization of α-olefins possible.

The imine compound which constitutes a basic invention (first invention) of the present invention is an imine compound represented by the following general formula (1).

[Chem. 1]

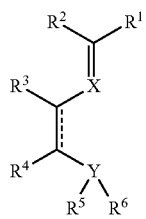

(1)

In formula (1), X represents a nitrogen atom, and Y represents a nitrogen atom or a phosphorus atom. $R^5$ and $R^6$ each independently are a hydrogen atom or a hydrocarbon group which has 1-30 carbon atoms and may contain one or more heteroatoms, at least one of $R^5$ and $R^6$ being a hydrocarbon group which contains two or more heteroatom-containing groups. $R^1$ to $R^4$ each independently represent a hydrogen atom, a hydrocarbon group which has 1-20 carbon atoms and may contain one or more heteroatoms, or a halogen atom. Two or more groups selected from among $R^1$ to $R^4$ may be linked to each other to form an alicyclic ring, an aromatic ring, or a heterocyclic ring which contains one or more heteroatoms selected from among oxygen, nitrogen, and sulfur atoms, in which each of the rings is a 5- to 8-membered ring which may have one or more substituents thereon.

A theoretical conjecture on why the desired catalytic performance can be produced by the complex structure specified in the present invention is given below.

The imine compound which constitutes a base of this invention is novel as a bidentate ligand, and is characterized by the electronic and steric structures of the ligand. These structures bring about a catalytic function in α-olefin polymerization. Specifically, the imine compound has a structure represented by general formula (1), and is used in the invention as a component of catalysts for olefin polymerization. This compound is used in combination with a co-catalyst or the like to form a catalyst for α-olefin polymerization.

The imine compound represented by general formula (1) in the invention is characterized in that $R^5$ and $R^6$ include heteroatom-containing groups. It is thought that due to the heteroatoms of $R^5$ and $R^6$, the Y shows enhanced donor characteristics with respect the central metal M to produce the effect of coordinating to the central metal M via the heteroatoms. It is also thought that due to the presence of substituents in the vicinity of the central metal, a β-hydrogen group elimination reaction, which results in a decrease in the molecular weight of the polymer, is less apt to occur. It can be presumed that the metal complex represented by general formula (2) is stabilized as a result and the polymer is inhibited from undergoing a chain transfer reaction, and that these features bring about the peculiarity of the present invention.

Meanwhile, the present invention considerably differs in constituent element (invention-specifying feature) from the prior-art inventions described in the patent documents and non-patent documents shown above, as stated hereinabove, and cannot be conceived from those prior-art documents. Specifically, a distinguishing feature of the present invention is the imine compound capable of forming a peculiar and novel bidentate ligand.

How the present invention has been achieved and the basic configuration and features of the invention have been summarized above. Here, when the overall configurations of the present invention are viewed perspectively, the present invention is considered to be configured of a group of the following invention units.

The imine compound represented by general formula (1) constitutes a basic invention (1) as stated above, and a metal complex obtained by reacting the imine compound of the basic invention (1) with a complex precursor which is a compound of a transition metal belonging to Groups 8 to 10 of the periodic table, i.e., a metal complex represented by the following general formula (2), constitutes a basic invention (2). The accompanying inventions are invention units which add further requirements to the basic inventions or show embodiments thereof. All these invention units are inclusively referred to as a group of inventions.

[Chem. 2]

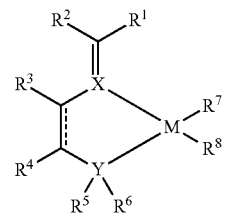

(2)

In general formula (2), M represents a transition metal belonging to Groups 8 to 10 of the periodic table. X represents a nitrogen atom, and Y represents a nitrogen atom or a phosphorus atom. $R^5$ and $R^6$ each independently are a hydrogen atom or a hydrocarbon group which has 1-30 carbon atoms and may contain one or more heteroatoms, at least one of $R^5$ and $R^6$ being a hydrocarbon group which contains two or more heteroatom-containing groups. $R^1$ to $R^4$, $R^7$, and $R^8$ each independently represent a hydrogen atom, a hydrocarbon group which has 1-20 carbon atoms and may contain one or more heteroatoms, or a halogen atom. Two or more groups selected from among $R^1$ to $R^4$, $R^7$, and $R^8$ may be linked to each other to form an alicyclic ring, an aromatic ring, or a heterocyclic ring which contains one or more heteroatoms selected from among oxygen, nitrogen, and sulfur atoms, in which each of the rings is a 5- to 8-membered ring which may have one or more substituents thereon.

Secondary inventions are: a catalyst component for olefin polymerization which includes the metal complex; and a catalyst for olefin polymerization characterized by including the following components (A) and (B) and optionally further containing the following component (C).

Component (A): the metal complex. Component (B): either a compound which reacts with component (A) to form an ion pair or an ion-exchange phyllosilicate. Component (C): an organoaluminum compound.

Other inventions include the catalyst for olefin polymerization wherein the component (B) is an aluminoxane and the catalyst for olefin polymerization wherein the component (B) is a boron compound, and further include a process for producing an olefin polymer which comprises polymerizing or copolymerizing one or more olefins in the presence of the catalyst for polymerization.

Furthermore, the other inventions include a process for producing an α-olefin/polar comonomer copolymer, the process comprising copolymerizing (a) α-olefin with (b) a polar comonomer in the presence of the catalyst for polymerization.

The other inventions still further include the process for producing an α-olefin/polar comonomer copolymer, wherein the polar comonomer (b) is a (meth)acrylic acid ester.

Effects of the Invention

According to the invention, it is possible to provide a ligand compound capable of forming a metal complex with which high-molecular-weight polymers of α-olefins can be produced and which further renders copolymerization of an α-olefin with an acrylic acid ester possible, and to further provide a polymerization catalyst for polyolefins that includes the ligand compound and a process for polymerizing an α-olefin using the catalyst.

It has been demonstrated by the data of the Examples which will be given later and by a comparison between the Examples and the Comparative Examples that the polymers produced by the present invention are higher in molecular weight than the polymer produced with a conventional imine complex.

It is thus expected that olefin-based polymers having a high molecular weight are efficiently produced, and the polymerization catalyst for polyolefins which is based on the metal complex of the invention and the process for olefin polymerization with the catalyst are exceedingly useful form an industrial standpoint.

MODES FOR CARRYING OUT THE INVENTION

The imine compound of the invention, the metal complex, the polymerization catalyst based on the complex, and the process for producing an olefin polymer using the catalyst are explained in detail below in order.
1. Imine Compound
(1) Basic Configuration The imine compound according to the invention is represented by the following general formula (1).

[Chem. 3]

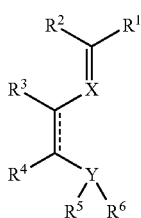

(1)

In the formula, X represents a nitrogen atom, and Y represents a nitrogen atom or a phosphorus atom. $R^5$ and $R^6$ each independently are a hydrogen atom or a hydrocarbon group which has 1-30 carbon atoms and may contain one or more heteroatoms, at least one of $R^5$ and $R^6$ being a hydrocarbon group which contains two or more heteroatom-containing groups. $R^1$ to $R^4$ each independently represent a hydrogen atom, a hydrocarbon group which has 1-20 carbon atoms and may contain one or more heteroatoms, or a halogen atom. Two or more groups selected from among $R^1$ to $R^4$ may be linked to each other to form an alicyclic ring, an aromatic ring, or a heterocyclic ring which contains one or more heteroatoms selected from among oxygen, nitrogen, and sulfur atoms, in which each of the rings is a 5- to 8-membered ring which may have one or more substituents thereon.

(2) With respect to $R^5$ and $R^6$

In the invention, $R^5$ and $R^6$ each independently are a hydrogen atom or a hydrocarbon group which has 1-30 carbon atoms and may contain one or more heteroatoms, at least one of $R^5$ and $R^6$ being a hydrocarbon group containing two or more heteroatom-containing groups. $R^5$ and $R^6$ lie around a metal M and sterically and/or electronically interact with the metal M. From the standpoint of producing this effect, it is preferable that $R^5$ and $R^6$ should be bulky. The number of carbon atoms of each of $R^5$ and $R^6$ is preferably 3-20, more preferably 6-20.

In $R^5$ and $R^6$, examples of the heteroatoms contained in the heteroatom-containing groups include oxygen, nitrogen, phosphorus, sulfur, selenium, silicon, fluorine, and boron. Preferred of these heteroatoms are oxygen, nitrogen, sulfur, and silicon. Examples of groups containing these heteroatoms include: oxygen-containing groups such as alkoxy groups, aryloxy groups, acyl groups, aroyl groups, and carboxylate groups; nitrogen-containing groups such as amino and amide groups; sulfur-containing groups such as thioalkoxy groups and thioaryloxy groups; phosphorus-containing groups such as a phosphino group; selenium-containing groups such as a selenyl group; silicon-containing groups such as trialkylsilyl groups, dialkylarylsilyl groups, and alkyldiarylsilyl groups; fluorine-containing groups such as fluoroalkyl groups and fluoroaryl groups; and boron-containing groups such as alkylboron groups and arylboron groups. Most preferred of these heteroatom-containing groups are alkoxy groups or aryloxy groups.

It is preferable that the heteroatoms contained in the heteroatom-containing groups should be ones capable of coordinating to transition metals. Specific examples of the heteroatom-containing groups which contain such a heteroatom capable of coordinating to transition metals include the following. Examples of oxygen-containing groups include methoxy, ethoxy, n-propoxy, isopropoxy, n-butoxy, t-butoxy, phenoxy, p-methylphenoxy, p-methoxyphenoxy, acetyl, benzoyl, acetoxy, ethylcarboxylate, t-butylcarboxylate, and phenylcarboxylate. Examples of nitrogen-containing groups include dimethylamino, diethylamino, di-n-propylamino, and cyclohexylamino. Examples of sulfur-containing groups include thiomethoxy, thioethoxy, thio-n-propoxy, thioisopropoxy, thio-n-butoxy, thio-t-butoxy, thiophenoxy, p-methylthiophenoxy, and p-methoxythiophenoxy. Examples of phosphorus-containing groups include dimethylphosphino, diethylphosphino, di-n-propylphosphino, and cyclohexylphosphino. Examples of selenium-containing groups include methylselenyl, ethylselenyl, n-propylselenyl, n-butylselenyl, t-butylselenyl, and phenylselenyl.

Although at least one of $R^5$ and $R^6$ has two or more heteroatom-containing groups, it is especially preferable that $R^5$ and $R^6$ each should contain two or more heteroatom-containing groups. With respect to combinations of $R^5$ and $R^6$, there are two cases, i.e., the case where $R^5$ and $R^6$ each have two or more heteroatom-containing groups and the case where either $R^5$ or $R^6$ has two or more heteroatom-containing groups and the remainder has one or less heteroatom-containing group. It is, however, preferable that $R^5$ and $R^6$ each should have two or more heteroatom-containing groups.

Although $R^5$ and $R^6$ in the invention each independently are a hydrogen atom or a hydrocarbon group which has 1-30 carbon atoms and may contain one or more heteroatoms, examples thereof include a hydrogen atom, linear hydrocarbon groups which may contain one or more heteroatoms, branched hydrocarbon groups which may contain one or more heteroatoms, alicyclic hydrocarbon groups which may contain one or more heteroatoms, and aryl groups which may contain one or more heteroatoms. As stated above, it is preferable that $R^5$ and $R^6$ should be bulky. Consequently, preferred of those examples are alicyclic hydrocarbon groups which may contain one or more heteroatoms or aryl groups which may contain one or more heteroatoms. Most preferred are aryl groups which may contain one or more heteroatoms. Examples of such aryl groups include phenyl, naphthyl, and anthracenyl.

In the case where any of the heteroatom-containing groups is bonded to the aromatic framework of each of the aryl groups of $R^5$ and $R^6$ in the invention, the mode of bonding may be one in which the heteroatom-containing group is directly bonded to the aromatic framework and one in which the heteroatom-containing group is bonded to the aromatic framework through a spacer such as one or more methylene groups. In the case where a heteroatom-containing group is bonded to the aromatic framework through one or more methylene groups, it is preferable that one methylene group should be interposed therebetween. With respect to substitution positions, preferred are the ortho positions to the Y-bonded carbon atom within each of the aromatic frameworks of $R^5$ and $R^6$. This configuration enables the heteroatoms within $R^5$ and $R^6$ to interact with the M.

Specific preferred examples of $R^5$ and $R^6$ include 2,6-dimethoxyphenyl, 2,4,6-trimethoxyphenyl, 4-methyl-2,6-dimethoxyphenyl, 4-t-butyl-2,6-dimethoxyphenyl, 1,3-dimethoxy-2-naphthyl, 2,6-diethoxyphenyl, 2,4,6-triethoxyphenyl, 4-methyl-2,6-diethoxyphenyl, 4-t-butyl-2,6-diethoxyphenyl, 1,3-diethoxy-2-naphthyl, 2,6-diphenoxyphenyl, 2,4,6-triphenoxyphenyl, 4-methyl-2,6-diphenoxyphenyl, 4-t-butyl-2,6-diphenoxyphenyl, 1,3-diphenoxy-2-naphthyl, 2,6-di(methoxymethyl)phenyl, 2,4,6-tri(methoxymethyl)phenyl, 4-methyl-2,6-di(methoxymethyl)phenyl, 4-t-butyl-2,6-di(methoxymethyl)phenyl, 1,3-di(methoxymethyl)-2-naphthyl, 2,6-di(phenoxymethyl)phenyl, 2,4,6-tri(phenoxymethyl)phenyl, 4-methyl-2,6-di(phenoxymethyl)phenyl, 4-t-butyl-2,6-di(phenoxymethyl)phenyl, 1,3-di(phenoxymethyl)-2-naphthyl, 2,6-di(2-methoxyethyl)phenyl, 2,4,6-tri(2-methoxyethyl)phenyl, 4-methyl-2,6-di(2-methoxyethyl)phenyl, 4-t-butyl-2,6-di(2-methoxyethyl)phenyl, 1,3-di(2-methoxyethyl)-2-naphthyl, 2,6-di(2-phenoxyethyl)phenyl, 2,4,6-tri(2-phenoxyethyl)phenyl, 4-methyl-2,6-di(2-phenoxyethyl)phenyl, 4-t-butyl-2,6-di(2-phenoxyethyl)phenyl, and 1,3-di(2-phenoxyethyl)-2-naphthyl.

(3) With Respect to $R^1$ to $R^4$ $R^1$ to $R^4$ each independently represent a hydrogen atom, a hydrocarbon group which has 1-20 carbon atoms and may contain one or more heteroatoms, or a halogen atom.

In $R^1$ to $R^4$, preferred examples of the halogen atom are fluorine, chlorine, and bromine. A more preferred substituent among these is chlorine.

In $R^1$ to $R^4$, examples of the heteroatoms contained in the hydrocarbon groups which have 1-20 carbon atoms and may contain one or more heteroatoms include oxygen, nitrogen, phosphorus, sulfur, selenium, silicon, fluorine, and boron. Preferred of these heteroatoms are oxygen, nitrogen, sulfur, and silicon. Examples of groups containing these heteroatoms include: oxygen-containing groups such as alkoxy groups, aryloxy groups, acyl groups, aroyl groups, and carboxylate groups; nitrogen-containing groups such as amino and amide groups; sulfur-containing groups such as thioalkoxy groups and thioaryloxy groups; phosphorus-containing groups such as a phosphino group; selenium-containing groups such as a selenyl group; silicon-containing groups such as trialkylsilyl groups, dialkylarylsilyl groups, and alkyldiarylsilyl groups; fluorine-containing groups such as fluoroalkyl groups and fluoroaryl groups; and boron-containing groups such as alkylboron groups and arylboron groups.

Specific examples of the heteroatom-containing groups are as follows. Examples of the oxygen-containing groups include methoxy, ethoxy, n-propoxy, isopropoxy, n-butoxy, t-butoxy, phenoxy, p-methylphenoxy, p-methoxyphenoxy, acetyl, benzoyl, acetoxy, ethylcarboxylate, t-butylcarboxylate, and phenylcarboxylate. Examples of the nitrogen-containing groups include dimethylamino, diethylamino, di-n-propylamino, and cyclohexylamino. Examples of the sulfur-containing groups include thiomethoxy, thioethoxy, thio-n-propoxy, thioisopropoxy, thio-n-butoxy, thio-t-butoxy, thiophenoxy, p-methylthiophenoxy, and p-methoxythiophenoxy. Examples of the phosphorus-containing groups include dimethylphosphino, diethylphosphino, di-n-propylphosphino, and cyclohexylphosphino. Examples of the selenium-containing groups include methylselenyl, ethylselenyl, n-propylselenyl, n-butylselenyl, t-butylselenyl, and phenylselenyl.

In $R^1$ to $R^4$, the hydrocarbon groups having 1-20 carbon atoms each preferably are an alkyl group, cycloalkyl group, alkenyl group, or aryl group.

Examples of the alkyl group and the cycloalkyl group include methyl, ethyl, 1-propyl, isopropyl, 1-butyl, isobutyl, t-butyl, 1-pentyl, 1-hexyl, 1-heptyl, 1-octyl, 1-nonyl, 1-decyl, tricyclohexylmethyl, 1,1-dimethyl-2-phenylethyl, 1,1-dimethylpropyl, 1,1,2-trimethylpropyl, 1,1-diethylpropyl, 1-phenyl-2-propyl, 1,1-dimethylbutyl, 2-pentyl, 3-pentyl, 2-hexyl, 3-hexyl, 2-ethylhexyl, 2-heptyl, 3-heptyl, 4-heptyl, 2-propylheptyl, 2-octyl, 3-nonyl, cyclopropyl, cyclobutyl, cyclopentyl, methylcyclopentyl, cyclohexyl, methylcyclohexyl, cycloheptyl, cyclooctyl, cyclododecyl, 1-adamantyl, 2-adamantyl, exo-norbornyl, endo-norbornyl, 2-bicyclo[2.2.2]octyl, nopinyl, decahydronaphthyl, menthyl, neomenthyl, neopentyl, and 5-decyl.

Preferred substituents among these are isopropyl, isobutyl, and cyclohexyl.

Examples of the alkenyl group include vinyl, allyl, butenyl, cinnamyl, and styryl.

Examples of the aryl group include phenyl, naphthyl, anthracenyl, and fluorenyl. Examples of substituents which can be present on the aromatic rings of these aryl groups are alkyl groups, aryl groups, fused aryl groups, phenylcyclohexyl, phenylbutenyl, tolyl, xylyl, and p-ethylphenyl.

A preferred substituent among these is phenyl. Especially preferred substituents among those examples are methyl, ethyl, and phenyl. In particular, methyl is more preferred. Those groups are mere examples, and it is obvious that the substituents are not limited to those examples.

Preferred examples of $R^1$ to $R^4$ include ones in which $R^3$ and $R^4$ have been linked to each other to form an alicyclic ring, an aromatic ring, or a heterocyclic ring which contains one or more heteroatoms selected from among oxygen, nitrogen, and sulfur atoms, and these rings each are a 5- to 8-membered ring which may have one or more substituents thereon. More preferred is the case where $R^3$ and $R^4$ have been linked to each other to form an aromatic ring, which may have one or more substituents thereon.

2. Metal Complex
(1) With Respect to Basic Configuration

The metal complex according to the invention is a metal complex obtained by reacting the imine compound with a complex precursor which is a compound of a transition metal belonging to Groups 8 to 10. Alternatively, the metal complex specifically is a metal complex represented by the following general formula (2).

[Chem. 4]

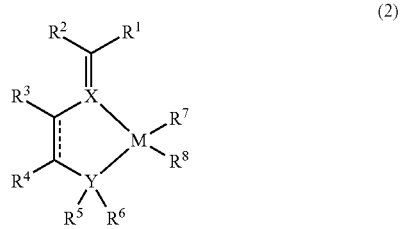

(2)

In general formula (2), M represents a transition metal belonging to Groups 8 to 10 of the periodic table. X represents a nitrogen atom, and Y represents a nitrogen atom or a phosphorus atom. $R^5$ and $R^6$ each independently are a hydrogen atom or a hydrocarbon group which has 1-30 carbon atoms and may contain one or more heteroatoms, at least one of $R^5$ and $R^6$ being a hydrocarbon group which contains two or more heteroatom-containing groups. $R^1$ to $R^4$, $R^7$, and $R^8$ each independently represent a hydrogen atom, a hydrocarbon group which has 1-20 carbon atoms and may contain one or more heteroatoms, or a halogen atom. Two or more groups selected from among $R^1$ to $R^4$, $R^7$, and $R^8$ may be linked to each other to form an alicyclic ring, an aromatic ring, or a heterocyclic ring which contains one or more heteroatoms selected from among oxygen, nitrogen, and sulfur atoms, in which each of the rings is a 5- to 8-membered ring which may have one or more substituents thereon.

$R^1$ to $R^6$ are the same as the substituents described above with regard to the imine compound represented by general formula (1).

M, which is an atom of a metal selected from the group consisting of transition metals belonging to Groups 8 to 10, preferably is a Group-10 transition metal.

Preferred examples thereof are nickel and palladium.
(2) With Respect to $R^7$ and $R^8$.

$R^7$ and $R^8$ each independently represent a hydrogen atom, a hydrocarbon group which has 1-20 carbon atoms and may contain one or more heteroatoms, or a halogen atom.

Preferred specific examples of $R^7$ and $R^8$ which are halogen atoms are fluorine, chlorine, and bromine. More preferred substituents among these are chlorine and bromine.

In $R^7$ and $R^8$, examples of the heteroatoms contained in the hydrocarbon groups which have 1-20 carbon atoms and may contain one or more heteroatoms include oxygen, nitrogen, phosphorus, sulfur, selenium, silicon, fluorine, and boron. Preferred of these heteroatoms are oxygen, silicon, and fluorine. Examples of groups containing these heteroatoms include: oxygen-containing groups such as alkoxy groups, aryloxy groups, acyl groups, aroyl groups, and carboxylate groups; nitrogen-containing groups such as amino and amide groups; sulfur-containing groups such as thioalkoxy groups and thioaryloxy groups; phosphorus-containing groups such as a phosphino group; selenium-containing groups such as a selenyl group; silicon-containing groups such as trialkylsilyl groups, dialkylarylsilyl groups, and alkyldiarylsilyl groups; fluorine-containing groups such as fluoroalkyl groups and fluoroaryl groups; and boron-containing groups such as alkylboron groups and arylboron groups.

Specific examples of the heteroatom-containing groups are as follows. Examples of the oxygen-containing groups include methoxy, ethoxy, n-propoxy, isopropoxy, n-butoxy, t-butoxy, phenoxy, p-methylphenoxy, p-methoxyphenoxy, acetyl, benzoyl, acetoxy, ethylcarboxylate, t-butylcarboxylate, and phenylcarboxylate. Examples of the nitrogen-containing groups include dimethylamino, diethylamino, di-n-propylamino, and cyclohexylamino. Examples of the sulfur-containing groups include thiomethoxy, thioethoxy, thio-n-propoxy, thioisopropoxy, thio-n-butoxy, thio-t-butoxy, thiophenoxy, p-methylthiophenoxy, and p-methoxythiophenoxy. Examples of the phosphorus-containing groups include dimethylphosphino, diethylphosphino, di-n-propylphosphino, and cyclohexylphosphino. Examples of the selenium-containing groups include methylselenyl, ethylselenyl, n-propylselenyl, n-butylselenyl, t-butylselenyl, and phenylselenyl.

In $R^7$ and $R^8$, the hydrocarbon groups having 1-20 carbon atoms each preferably are an alkyl group, cycloalkyl group, alkenyl group, or aryl group.

Examples of the alkyl group and the cycloalkyl group include methyl, ethyl, 1-propyl, isopropyl, 1-butyl, isobutyl, t-butyl, 1-pentyl, 1-hexyl, 1-heptyl, 1-octyl, 1-nonyl, 1-decyl, tricyclohexylmethyl, 1,1-dimethyl-2-phenylethyl, 1,1-dimethylpropyl, 1,1,2-trimethylpropyl, 1,1-diethylpropyl, 1-phenyl-2-propyl, 1,1-dimethylbutyl, 2-pentyl, 3-pentyl, 2-hexyl, 3-hexyl, 2-ethylhexyl, 2-heptyl, 3-heptyl, 4-heptyl, 2-propylheptyl, 2-octyl, 3-nonyl, cyclopropyl, cyclobutyl, cyclopentyl, methylcyclopentyl, cyclohexyl, methylcyclohexyl, cycloheptyl, cyclooctyl, cyclododecyl, 1-adamantyl, 2-adamantyl, exo-norbornyl, endo-norbornyl, 2-bicyclo[2.2.2]octyl, nopinyl, decahydronaphthyl, menthyl, neomenthyl, neopentyl, and 5-decyl.

Preferred substituents among these are isopropyl, isobutyl, and cyclohexyl.

Examples of the alkenyl group include vinyl, allyl, butenyl, cinnamyl, and styryl.

Examples of the aryl group include phenyl, naphthyl, anthracenyl, and fluorenyl. Examples of substituents which can be present on the aromatic rings of these aryl groups are alkyl groups, aryl groups, fused aryl groups, phenylcyclohexyl, phenylbutenyl, tolyl, xylyl, and p-ethylphenyl.

A preferred substituent among these is phenyl. Especially preferred substituents among those examples are methyl, ethyl, and phenyl. In particular, methyl is more preferred. Those groups are mere examples, and it is obvious that the substituents are not limited to those examples.
(3) Specific Examples of the Metal Complex Preferred specific examples of the metal complex according to the invention include the following nickel complexes. The following are mere examples, and it is obvious that the metal complex is not limited to the following examples, in which Me denotes methyl, Et denotes ethyl, iPr denotes isopropyl, tBu denotes tert-butyl, and Ph denotes phenyl.

[Chem. 5]
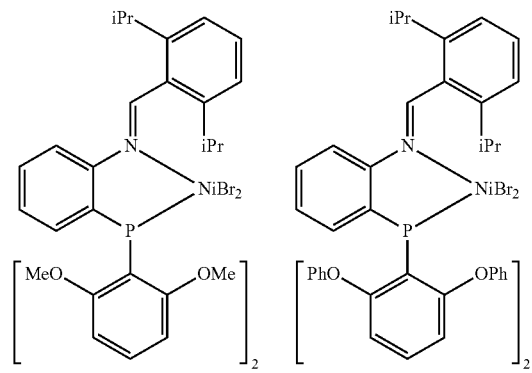
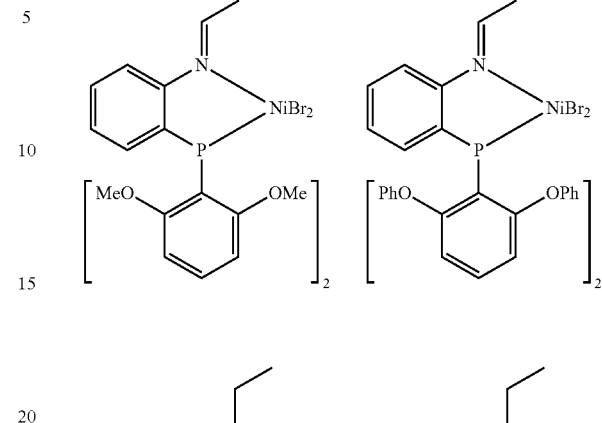
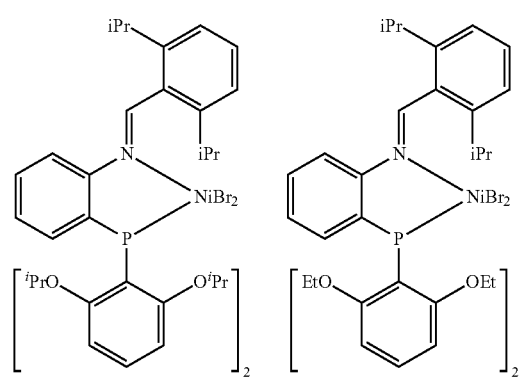
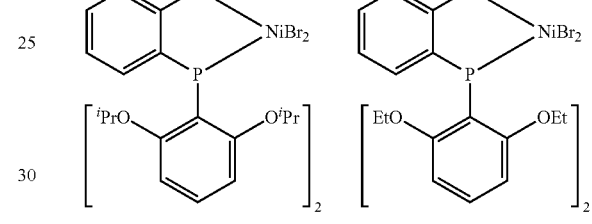
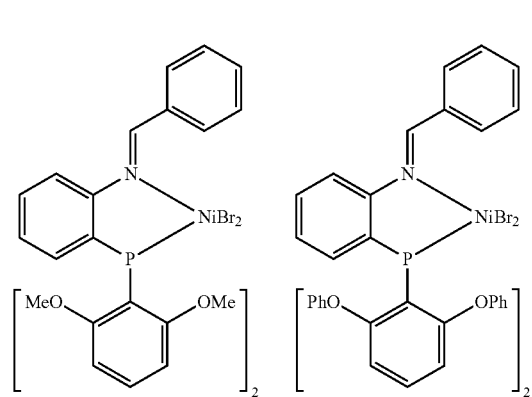
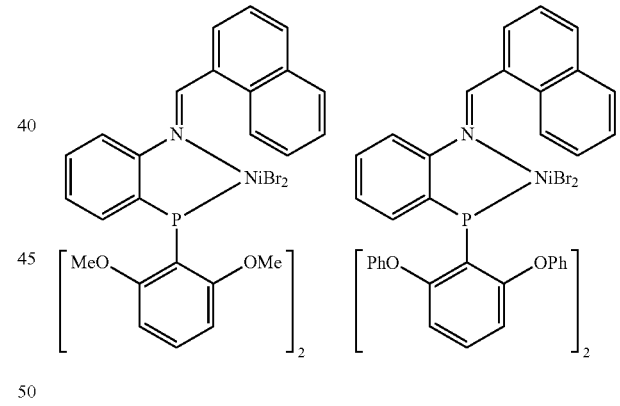
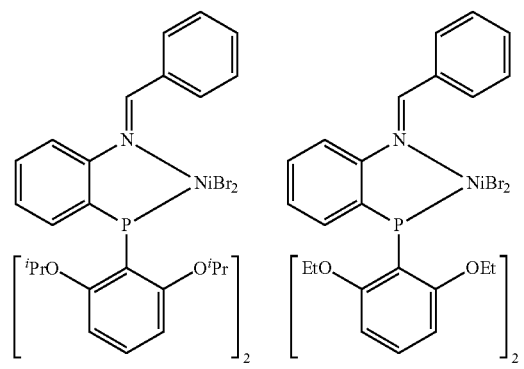
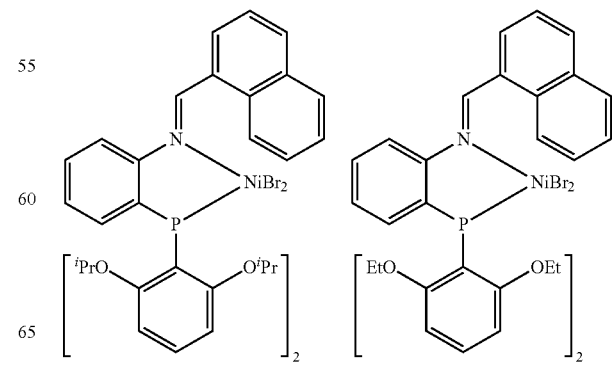

-continued

[Chem. 6]

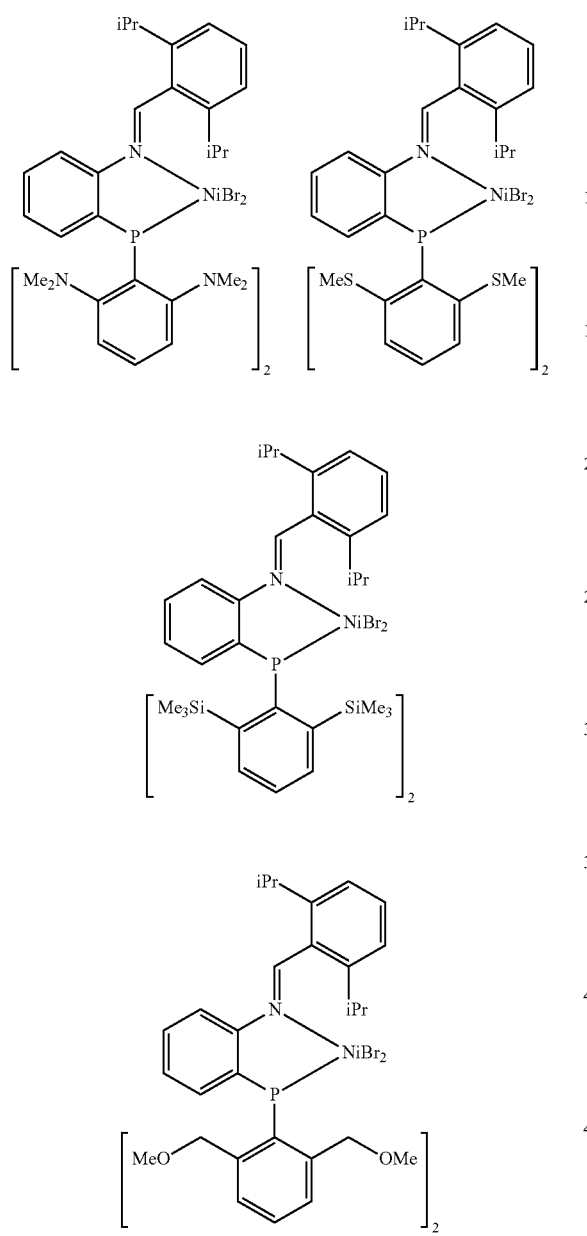

[Chem. 7]

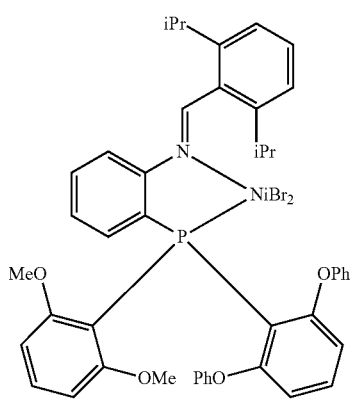

-continued

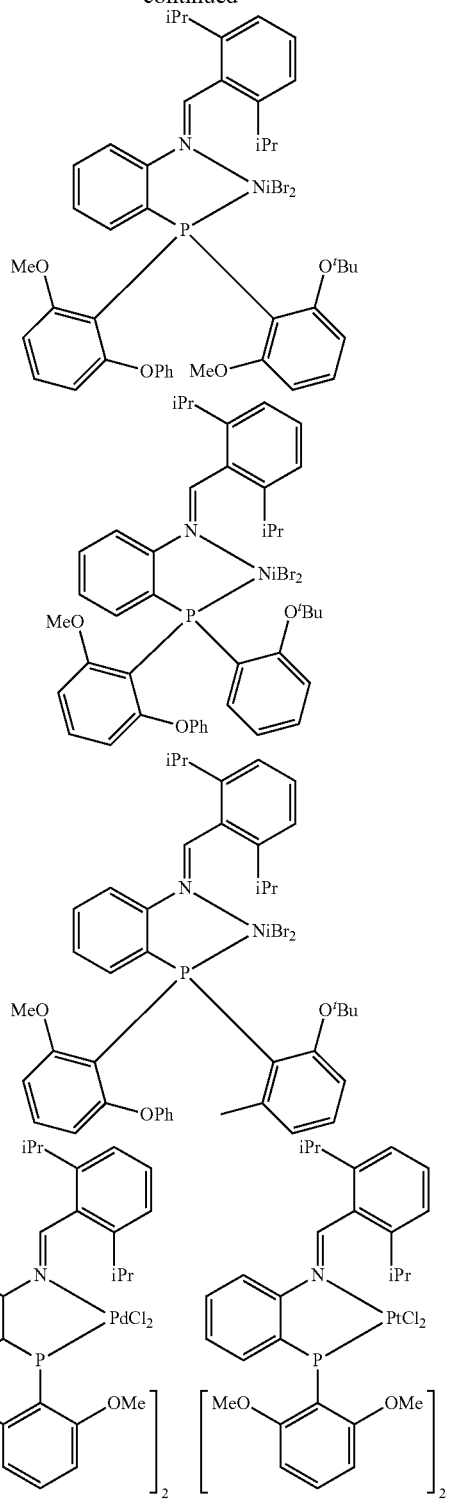

3. Synthesis of the Imine Compound and of the Metal Complex Through Reaction of the Imine (1) Basic Synthesis Route The imine compound according to the invention can be synthesized through any desired imine synthesis route. Although a synthesis route for obtaining the metal complex by reacting the imine can be determined at will in view of the structure of the desired compound, examples thereof include a route in which the imine compound as a starting material is reacted with a complex precursor.

(2) Complex Precursor

The complex precursor according to the invention, which is a compound of a transition metal belonging to Groups 8 to 10, preferably is a complex of a Group-10 transition metal.

Preferred examples thereof include nickel(II) fluoride, nickel(II) chloride, nickel(II) bromide, nickel(II) iodide, nickel(II) chloride (1,2-dimethoxyethane) complex, nickel (II) bromide (1,2-dimethoxyethane) complex, nickel(II) acetate, palladium(II) chloride, palladium(II) bromide, palladium(II) iodide, palladium(II) chloride bis(acetonitrile) complex, palladium(II) chloride bis(benzonitrile) complex, allylpalladium chloride(II), palladium acetate(II), palladium trifluoroacetate(II), platinum(II) chloride, platinum(II) bromide, and platinum(II) iodide.

(3) Reaction with Complex Precursor

The amount of the complex precursor to be used in the invention is in the range of usually 0.5-3 mol, preferably 0.7-1.5 mol, per mole of the imine compound represented by general formula (1).

The complex synthesis reaction may be conducted in the reactor to be used for the copolymerization with an α-olefin, or may be conducted in a vessel which is not the reactor. After complex formation, the metal complex may be isolated and used in a catalyst, or may be used in a catalyst without being isolated.

4. Catalyst for Olefin Polymerization

The metal complex of the invention obtained by reaction with the imine constitutes a catalyst component for olefin polymerization, and this catalyst component can be used in catalysts for olefin polymerization. For example, it is preferred to use the metal complex in the catalyst for olefin polymerization explained below, which includes the metal complex as component (A).

(1) Components of the Catalyst for Olefin Polymerization

The catalyst for olefin polymerization of the invention includes the following components (A) and (B) and optionally includes the following component (C).

Component (A): either a metal complex obtained by reacting the imine compound represented by general formula (1) with the complex precursor or a metal complex represented by general formula (2)

Component (B): either a compound which reacts with component (A) to form an ion pair or an ion-exchange phyllosilicate Component (C): an organoaluminum compound (2) With Respect to the Components Component (A)

Component (A) is either a metal complex obtained by reacting the imine compound represented by general formula (1) with the complex precursor or a metal complex represented by general formula (2), and two or more such complexes of the same or different kinds may be used.

Component (B)

Component (B) is either a compound which reacts with component (A) to form an ion pair or an ion-exchange phyllosilicate.

An example of component (B) is organoaluminumoxy compounds. The organoaluminumoxy compounds each have one or more Al—O—Al bonds in the molecule, and the number of these bonds is in the range of usually 1-100, preferably 1-50. Such an organoaluminumoxy compound usually is a product obtained by reacting an organoaluminum compound with water.

The reaction between an organoaluminum with water is usually conducted in an inert hydrocarbon (solvent). As the inert hydrocarbon, use can be made of aliphatic hydrocarbons, alicyclic hydrocarbons, and aromatic hydrocarbons, such as pentane, hexane, heptane, cyclohexane, methylcyclohexane, benzene, toluene, and xylene. It is, however, preferred to use an aliphatic hydrocarbon or an aromatic hydrocarbon.

As the organoaluminum compound for preparing the organoaluminumoxy compound, any of compounds represented by the following general formula (3) can be used. However, it is preferred to use a trialkylaluminum.

$$(R^9)_t Al(Z^1)_{(3-t)} \qquad \text{general formula (3)}$$

(In general formula (3), $R^9$ represents a hydrocarbon group having 1-18, preferably 1-12 carbon atoms, such as an alkyl group, alkenyl group, aryl group, or aralkyl group, $Z^1$ represents a hydrogen atom or a halogen atom, and t represents an integer satisfying $1 \leq t \leq 3$.)

The alkyl groups of the trialkylaluminum may be any of methyl, ethyl, propyl, isopropyl, butyl, isobutyl, pentyl, hexyl, octyl, decyl, dodecyl, and the like. However, it is especially preferable that the alkyl groups should be methyl. Two or more such organoaluminum compounds can be used as a mixture thereof.

It is preferable that the ratio in which water is reacted with an organoaluminum compound (water/Al molar ratio) should be from 0.25/1 to 1.2/1, in particular, from 0.5/1 to 1/1. The reaction temperature is in the range of usually −70 to 100° C., preferably −20 to 20° C. The reaction time is selected from the range of usually 5 minutes to 24 hours, preferably 10 minutes to 5 hours. As the water to be reacted, use can be made of not only mere water but also the crystal water contained in copper sulfate hydrates, aluminum sulfate hydrates, and the like or even an ingredient capable of yielding water in the reaction system.

Of the organoaluminumoxy compounds, ones obtained by reacting an alkylaluminum with water are usually called aluminoxanes. In particular, methylaluminoxane (including ones consisting substantially of methylaluminoxane (MAO)) is suitable as the organoaluminumoxy compound.

It is, of course, possible to use two or more of these organoaluminumoxy compounds in combination. Furthermore, any of the organoaluminumoxy compounds may be used in the form of a solution obtained by dissolving or dispersing the compound in any of the inert hydrocarbon solvents shown above.

Other examples of component (B) include borane compounds and borate compounds. More specific examples of the borane compounds include triphenylborane, tri(o-tolyl) borane, tri(p-tolyl)borane, tri(m-tolyl)borane, tri(o-fluorophenyl)borane, tri(p-fluorophenyl)borane, tris(m-fluorophenyl)borane, tris(2,5-difluorophenyl)borane, tris(3,5-difluorophenyl)borane, tris(4-trifluoromethylphenyl)borane, tris(3,5-bis(trifluoromethyl)phenyl)borane, tris(2,6-bis(trifluoromethyl)phenyl)borane, tris(pentafluorophenyl)borane, tris(perfluoronaphthyl)borane, tris(perfluorobiphenyl)borane, tris(perfluoroanthryl)borane, and tris(perfluorobinaphthyl)borane.

More preferred of these are tris(3,5-bis(trifluoromethyl) phenyl)borane, tris(2,6-bis(trifluoromethyl)phenyl)borane, tris(pentafluorophenyl)borane, tris(perfluoronaphthyl)borane, tris(perfluorobiphenyl)borane, tris(perfluoroanthryl) borane, and tris(perfluorobinaphthyl)borane. Even more preferred examples are tris(2,6-bis(trifluoromethyl)phenyl)

borane, tris(pentafluorophenyl)borane, tris(perfluoronaphthyl)borane, and tris(perfluorobiphenyl)borane.

Meanwhile, specific examples of the borate compounds are as follows. A first example thereof is compounds represented by the following general formula (4).

$$[L^1\text{-}H]^+[B(R^{10})(R^{11})(Z^2)(Z^3)]^-  \quad \text{general formula (4)}$$

In general formula (4), $L^1$ is a neutral Lewis base, H is a hydrogen atom, and $[L^1\text{-}H]$ is a Brønsted acid such as an ammonium, anilinium, or phosphonium.

Examples of the ammonium include trialkyl-substituted ammoniums such as trimethylammonium, triethylammonium, tripropylammonium, tributylammonium, and tri(n-butyl)ammonium and dialkylammoniums such as di(n-propyl)ammonium and dicyclohexylammonium.

Examples of the anilinium include N,N-dialkylaniliniums such as N,N-dimethylanilinium, N,N-diethylanilinium, and N,N-2,4,6-pentamethylanilinium.

Furthermore, examples of the phosphonium include triarylphosphoniums and trialkylphosphoniums, such as triphenylphosphonium, tributylphosphonium, tris(methylphenyl)phosphonium, and tris(dimethylphenyl)phosphonium.

In general formula (4), $R^{10}$ and $R^{11}$ are the same or different, aromatic or substituted aromatic hydrocarbon groups which each contain 6-20, preferably 6-16, carbon atoms, and which may have been linked to each other by a bridging group. Preferred as the substituents of the substituted aromatic hydrocarbon groups are alkyl groups represented by methyl, ethyl, propyl, isopropyl, and the like and halogen atoms such as fluorine, chlorine, bromine, and iodine. $Z^2$ and $Z^3$ each are a hydride group, a halide group, a hydrocarbon group containing 1-20 carbon atoms, or a substituted hydrocarbon group which contains 1-20 carbon atoms and in which one or more of the hydrogen atoms have each been replaced with a halogen atom.

Specific examples of the compounds represented by general formula (4) include tributylammonium tetrakis(pentafluorophenyl) borate, tributylammonium tetrakis(2,6-bis(trifluoromethyl)phenyl) borate, tributylammonium tetrakis(3,5-bis(trifluoromethyl)phenyl) borate, tributylammonium tetrakis(2,6-difluorophenyl) borate, tributylammonium tetrakis(perfluoronaphthyl) borate, dimethylanilinium tetrakis(pentafluorophenyl) borate, dimethylanilinium tetrakis(2,6-bis(trifluoromethyl)phenyl) borate, dimethylanilinium tetrakis(3,5-bis(trifluoromethyl)phenyl) borate, dimethylanilinium tetrakis(2,6-difluorophenyl) borate, dimethylanilinium tetrakis(perfluoronaphthyl) borate, triphenylphosphonium tetrakis(pentafluorophenyl) borate, triphenylphosphonium tetrakis(2,6-bis(trifluoromethyl)phenyl) borate, triphenylphosphonium tetrakis(3,5-bis(trifluoromethyl)phenyl) borate, triphenylphosphonium tetrakis(2,6-difluorophenyl) borate, triphenylphosphonium tetrakis(perfluoronaphthyl) borate, trimethylammonium tetrakis(2,6-bis(trifluoromethyl)phenyl) borate, triethylammonium tetrakis(pentafluorophenyl) borate, triethylammonium tetrakis(2,6-bis(trifluoromethyl)phenyl) borate, triethylammonium tetrakis(perfluoronaphthyl) borate, tripropylammonium tetrakis(pentafluorophenyl) borate, tripropylammonium tetrakis(2,6-bis(trifluoromethyl)phenyl) borate, tripropylammonium tetrakis(perfluoronaphthyl) borate, tripropylammonium tetrakis(pentafluorophenyl) borate, and dicyclohexylammonium tetraphenyl borate.

Preferred of these are tributylammonium tetrakis(pentafluorophenyl) borate, tributylammonium tetrakis(2,6-bis(trifluoromethyl)phenyl) borate, tributylammonium tetrakis(3,5-bis(trifluoromethyl)phenyl) borate, tributylammonium tetrakis(perfluoronaphthyl) borate, dimethylanilinium tetrakis(pentafluorophenyl) borate, dimethylanilinium tetrakis(2,6-bis(trifluoromethyl)phenyl) borate, dimethylanilinium tetrakis(3,5-bis(trifluoromethyl)phenyl) borate, and dimethylanilinium tetrakis(perfluoronaphthyl) borate.

A second example of the borate compounds is represented by the following general formula (5).

$$[L^2]^+[B(R^{10})(R^{11})(Z^2)(Z^3)]^- \quad \text{general formula (5)}$$

In general formula (5), examples of $L^2$ include a carbo cation, methyl cation, ethyl cation, propyl cation, isopropyl cation, butyl cation, isobutyl cation, tert-butyl cation, pentyl cation, tropinium cation, benzyl cation, trityl cation, sodium cation, and proton. $R^{10}$, $R^{11}$, $Z^2$, and $Z^3$ are the same as defined above with regard to general formula (4).

Specific examples of these compounds include trityl tetraphenyl borate, trityl tetra(o-tolyl) borate, trityl tetra(p-tolyl) borate, trityl tetra(m-tolyl) borate, trityl tetra(o-fluorophenyl) borate, trityl tetra(p-fluorophenyl) borate, trityl tetra(m-fluorophenyl) borate, trityl tetrakis(3,5-difluorophenyl) borate, trityl tetrakis(pentafluorophenyl) borate, trityl tetrakis(2,6-bis(trifluoromethyl)phenyl) borate, trityl tetrakis(3,5-bis(trifluoromethyl)phenyl) borate, trityl tetrakis(perfluoronaphthyl) borate, tropinium tetraphenyl borate, tropinium tetra(o-tolyl) borate, tropinium tetra(p-tolyl) borate, tropinium tetra(m-tolyl) borate, tropinium tetra(o-fluorophenyl) borate, tropinium tetra(p-fluorophenyl) borate, tropinium tetra(m-fluorophenyl) borate, tropinium tetrakis(3,5-difluorophenyl) borate, tropinium tetrakis(pentafluorophenyl) borate, tropinium tetrakis(2,6-bis(trifluoromethyl)phenyl) borate, tropinium tetrakis(3,5-bis(trifluoromethyl)phenyl) borate, tropinium tetrakis(perfluoronaphthyl) borate, $NaBPh_4$, $NaB(o\text{-}CH_3C_6H_4)_4$, $NaB(p\text{-}CH_3C_6H_4)_4$, $NaB(m\text{-}CH_3C_6H_4)_4$, $NaB(o\text{-}FC_6H_4)_4$, $NaB(p\text{-}FC_6H_4)_4$, $NaB(m\text{-}FC_6H_4)_4$, $NaB(3,5\text{-}F_2C_6H_3)_4$, $NaB(C_6F_5)_4$, $NaB(2,6\text{-}(CF_3)_2C_6H_3)_4$, $NaB(3,5\text{-}(CF_3)_2C_6H_3)_4$, $NaB(C_{10}F_7)_4$, $HBPh_4 \cdot 2(\text{diethyl ether})$, $HB(2,6\text{-}(CF_3)_2C_6H_3)_4 \cdot 2(\text{diethyl ether})$, $HB(3,5\text{-}(CF_3)_2C_6H_3)_4 \cdot 2(\text{diethyl ether})$, and $HB(C_{10}H_7)_4 \cdot 2(\text{diethyl ether})$.

Preferred of these are trityl tetrakis(pentafluorophenyl) borate, trityl tetrakis(2,6-bis(trifluoromethyl)phenyl) borate, trityl tetrakis(3,5-bis(trifluoromethyl)phenyl) borate, trityl tetrakis(perfluoronaphthyl) borate, tropinium tetrakis(pentafluorophenyl) borate, tropinium tetrakis(2,6-bis(trifluoromethyl)phenyl) borate, tropinium tetrakis(3,5-bis(trifluoromethyl)phenyl) borate, tropinium tetrakis(perfluoronaphthyl) borate, $NaB(C_6F_5)_4$, $NaB(2,6\text{-}(CF_3)_2C_6H_3)_4$, $NaB(3,5\text{-}(CF_3)_2C_6H_3)_4$, $NaB(C_{10}F_7)_4$, $HB(C_6F_5)_4 \cdot 2(\text{diethyl ether})$, $HB(2,6\text{-}(CF_3)_2C_6H_3)_4 \cdot 2(\text{diethyl ether})$, $HB(3,5\text{-}(CF_3)_2C_6H_3)_4 \cdot 2(\text{diethyl ether})$, and $HB(C_{10}H_7)_4 \cdot 2(\text{diethyl ether})$.

More preferred of these are trityl tetrakis(pentafluorophenyl) borate, trityl tetrakis(2,6-bis(trifluoromethyl)phenyl) borate, tropinium tetrakis(pentafluorophenyl) borate, tropinium tetrakis(2,6-bis(trifluoromethyl)phenyl) borate, $NaB(C_6F_5)_4$, $NaB(2,6\text{-}(CF_3)_2C_6H_3)_4$, $HB(C_6F_5)_4 \cdot 2(\text{diethyl ether})$, $HB(2,6\text{-}(CF_3)_2C_6H_3)_4 \cdot 2(\text{diethyl ether})$, $HB(3,5\text{-}(CF_3)_2C_6H_3)_4 \cdot 2(\text{diethyl ether})$, and $HB(C_{10}H_7)_4 \cdot 2(\text{diethyl ether})$.

Examples of component (B) further include ion-exchange phyllosilicates. The term "ion-exchange phyllosilicate" (hereinafter sometimes referred to simply as "silicate") means a silicate compound which has a crystalline structure made up of sheets each formed by ionic bonds or the like, the sheets having been stacked in parallel with each other by bonding power, and which can contain exchangeable ions. Various silicates are known, and are described in detail in SHIROZU Haruo, *Nendo Kōbutsu Gaku*, Asakura Publishing Co., Ltd. (1995).

Silicates which are preferred for use as component (B) in the invention are ones belonging to the smectite group, and examples thereof include montmorillonite, sauconite, beidellite, nontronite, saponite, hectorite, and stevensite. Of these, montmorillonite is preferred from the standpoint of enhancing the polymerization activity of copolymer portions to obtain a heightened molecular weight.

Since most natural silicates occur as main components of clay minerals, there frequently are cases where ion-exchange phyllosilicates contain other substances as impurities (e.g., quartz and cristobalite). The smectite-group silicate to be used in the invention may contain impurities.

As component (B), use can be made of a mixture of the organoaluminumoxy compound, the borane compound or borate compound, and the ion-exchange phyllosilicate. Any of these substances may be used alone, or two or more thereof may be used.

Component (C)

An example of the organoaluminum compound to be used as component (C) is represented by the following general formula.

$$Al(R^{12})_a Z^4_{(3-a)} \qquad \text{general formula (6)}$$

In general formula (6), $R^{12}$ represents a hydrocarbon group having 1-20 carbon atoms, $Z^4$ represents a hydrogen atom, a halogen atom, an alkoxy group, or a siloxy group, and symbol a represents a number larger than 0 but not larger than 3.

Specific examples of the organoaluminum compounds represented by general formula (6) include trialkylaluminums such as trimethylaluminum, triethylaluminum, tripropylaluminum, and triisobutylaluminum and halogen- or alkoxy-containing alkylaluminum, such as diethylaluminum monochloride and diethylaluminum monomethoxide.

Preferred of these is triisobutylaluminum. Two or more of those organoaluminum compounds may be used in combination. Furthermore, those aluminum compounds may be modified with an alcohol, phenol, etc. Examples of these modifiers include methanol, ethanol, 1-propanol, isopropanol, butanol, phenol, 2,6-dimethylphenol, and 2,6-di-t-butylphenol. Preferred examples thereof are 2,6-dimethylphenol and 2,6-di-t-butylphenol.

(3) Methods for Preparing the Catalyst

In the preparation of the catalyst for olefin polymerization according to the invention, methods for contacting components (A) and (B) and optionally component (C) are not particularly limited. However, examples thereof include the following methods.

(i) A method in which component (A) and component (B) are brought into contact with each other and component (C) is added thereafter.

(ii) A method in which component (A) and component (C) are brought into contact with each other and component (B) is added thereafter.

(iii) A method in which component (B) and component (C) are brought into contact with each other and component (A) is added thereafter.

(iv) A method in which components (A), (B), and (C) are simultaneously brought into contact with each other.

Furthermore, in each component, different components may be used as a mixture or may be separately contacted in a different order. This contact may be performed not only during the catalyst preparation but also during preliminary polymerization of an olefin or during polymerization of an olefin.

Moreover, a component may be brought, by installments, into contact with other components, for example, in such a manner that component (B) and component (C) are contacted with each other and a mixture of component (A) and component (C) is added thereafter.

It is preferable that the contact of components (A), (B), and (C) should be conducted in an inert hydrocarbon solvent such as pentane, hexane, heptane, toluene, or xylene in an inert gas such as nitrogen. The contact can be conducted at a temperature between −20° C. and the boiling point of the solvent, and it is especially preferred to perform the contact at a temperature between room temperature and the boiling point of the solvent.

5. Polymerization Methods (1) Monomers (a) α-Olefins

Ingredient (a) in the invention is one or more α-olefins represented by the general formula $CH_2=CHR^{13}$. $R^{13}$ is a hydrogen atom or a hydrocarbon group which has 1-20 carbon atoms and which may have a branch, a ring, and/or an unsaturated bond. In case where the number of carbon atoms of $R^{13}$ is larger than 20, this α-olefin tends to have insufficient polymerization activity. Because of this, preferred examples of ingredient (a) among these include α-olefins in which $R^{13}$ is a hydrogen atom or a hydrocarbon group having 1-10 carbon atoms.

More preferred examples of ingredient (a) include ethylene, propylene, 1-butene, 1-pentene, 1-hexene, 1-oxtene, 1-decene, 3-methyl-1-butene, 4-methyl-1-pentene, vinylcyclohexene, and styrene. One ingredient (a) may be used, or a plurality of ingredients (a) may be used in combination.

Besides the ingredient (a), other monomer ingredients may be contained such as cycloolefins and internal olefins. Preferred ingredients include norbornene, 5-ethylidene-2-norbornene, 5-vinyl-2-norbornene, norbornadiene, cyclopentene, cyclohexene, cyclopentadiene, and the like.

(b) Polar Comonomers

The polar comonomers to be used in the invention are compounds which each have in the molecule a carbon-carbon double bond and a substituent (polar group) containing an atom having an electronegativity different from that of the carbon atom. Examples of the polar group include halogens, hydroxy group (—OH), amino group (—NH$_2$), imino group (=NH), nitro group (—NO$_2$), carboxyl group (—COOH), formyl group (—CHO), alkoxy groups (—OR), ester groups (—COOR), nitrile group (—CN), ether group (—O—), silyl group (—SiH$_3$), alkylsilyl groups (SiR$_3$), alkoxysilyl groups (—Si(OR)$_3$), carbonyl group (=CO), epoxy group, acid anhydride groups, and ammonium group (—N$^+$H$_3$).

Preferred examples of ingredient (b) in the invention include (meth)acrylic acid esters represented by the general formula $CH_2=C(R^{14})CO_2(R^{15})$. $R^{14}$ is a hydrogen atom or a hydrocarbon group which has 1-10 carbon atoms and which may have a branch, a ring, and/or an unsaturated bond. $R^{15}$ is a hydrocarbon group which has 1-30 carbon atoms and which may have a branch, a ring, and/or an unsaturated bond. $R^{15}$ may contain one or more heteroatoms at any desired positions therein.

In case where the number of carbon atoms of $R^{14}$ is 11 or larger, this compound tends to have insufficient polymerization activity. Consequently, although $R^{14}$ is a hydrogen atom or a hydrocarbon group having 1-10 carbon atoms, preferred examples of ingredient (b) include (meth)acrylic acid esters in which $R^{14}$ is a hydrogen atom or a hydrocarbon group having 1-5 carbon atoms. More preferred examples of ingredient (b) include methacrylic acid esters in which $R^{14}$ is methyl or acrylic acid esters in which $R^{14}$ is a hydrogen atom. Likewise, in case where the number of carbon atoms of $R^{15}$ exceeds 30, this monomer tends to have reduced polymerization activity. Consequently, although the number of carbon atoms of $R^{15}$ is 1-30. $R^{15}$ has preferably 1-12 carbon atoms, more preferably 1-8 carbon atoms.

Examples of the heteroatoms which may be contained in $R^{15}$ include oxygen, sulfur, selenium, phosphorus, nitrogen, silicon, fluorine, and boron. Preferred of these heteroatoms are oxygen, silicon, and fluorine. More preferred is oxygen. It is also preferable that $R^{15}$ should contain no heteroatom.

Even more preferred examples of ingredient (b) include methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, pentyl (meth)acrylate, hexyl (meth)acrylate, cyclohexyl (meth)acrylate, octyl (meth)acrylate, 2-ethylhexyl (meth) acrylate, nonyl (meth)acrylate, decyl (meth)acrylate, dodecyl (meth)acrylate, phenyl (meth)acrylate, toluyl (meth)acrylate, benzyl (meth)acrylate, hydroxyethyl (meth)acrylate, 1,4-cyclohexanedimethanol mono(meth)acrylate, 4-hydroxybutyl (meth)acrylate glycidyl ether (4-HBAGE), 3-(trimethoxysilyl)propyl (meth)acrylate, (meth)acrylic acid polyethylene glycol esters (EEEA), dimethylaminoethyl (meth)acrylate, diethylaminoethyl (meth)acrylate, 2-aminoethyl (meth)acrylate, 2-methoxyethyl (meth)acrylate, 3-methyoxypropyl (meth)acrylate, glycidyl (meth)acrylate, (meth)acrylic acid/ethylene oxide, trifluoromethyl (meth)acrylate, 2-trifluoromethylethyl (meth)acrylate, perfluoroethyl (meth)acrylate, (meth)acrylamide, dimethyl(meth)acrylamide, 2-hydroxybutyl (meth)acrylate, and 4-hydroxybutyl (meth)acrylate. One ingredient (b) may be used, or a plurality of ingredients (b) may be used in combination.

(2) Polymerization Methods

In the invention, the polymerization reaction can be conducted in the presence of the supported catalyst described above preferably by slurry polymerization or vapor phase polymerization. In the case of slurry polymerization, ethylene or the like may be polymerized in the presence or absence of an inert hydrocarbon solvent selected from among aliphatic hydrocarbons such as isobutane, hexane, and heptane, aromatic hydrocarbons such as benzene, toluene, and xylene, alicyclic hydrocarbons such as cyclohexane and methylcyclohexane, and the like while keeping the system substantially free from oxygen, water, etc. It is a matter of course that a liquid monomer such as liquid ethylene or liquid propylene is also usable as a solvent.

Polymerization conditions are usually as follows. The temperature is preferably 0-250° C., more preferably 20-110° C., even more preferably 50-100° C. The pressure is in the range of preferably from normal pressure to 10 MPa, more preferably from normal pressure to 4 MPa. The polymerization period is preferably 5 minutes to 10 hours, more preferably 5 minutes to 5 hours.

An ingredient for water removal, i.e., a so-called scavenger, may be added to the polymerization system, and the polymerization can be carried out therewith without arousing any problem. As the scavenger, use may be made of organoaluminum compounds such as trimethylaluminum, triethylaluminum, and triisobutylaluminum, the organoaluminumoxy compounds shown hereinabove, modified organoaluminum compounds containing a branched alkyl, organozinc compounds such as diethylzinc and dibutylzinc, organomagnesium compounds such as diethylmagnesium, dibutylmagnesium, and ethylbutylmagnesium, Grignard compounds such as ethylmagnesium chloride and butylmagnesium chloride, and the like.

Preferred of these are triethylaluminum, triisobutylaluminum, and ethylbutylmagnesium. Especially preferred is triethylaluminum.

A multistage polymerization method including two or more stages differing in polymerization conditions can also be used for the polymerization without raising difficulties.

EXAMPLES

The present invention will be explained below in detail by reference to Examples to demonstrate the rationality and meaningfulness of the configuration of the invention and the superiority thereof over prior-art techniques.

1. Evaluation Method (1) Weight-Average Molecular Weight Mw, Number-Average Molecular Weight Mn, and Molecular Weight Distribution Mw/Mn:

The molecular weights and the distribution were determined through the following GPC measurement.

First, a sample was introduced in an amount of about 20 (mg) into a vial for pretreatment device PL-SP260VS for high-temperature GPC, manufactured by Polymer Laboratories Ltd. o-Dichlorobenzene containing BHT as a stabilizer (BHT concentration=0.5 g/L) was added thereto to adjust the polymer concentration to 0.1 (% by weight). The resultant mixture was heated to 135° C. in the pretreatment device PL-SP260VS for high-temperature GPC to dissolve the polymer, and the solution was filtered with a glass filter to prepare a specimen.

In the GPC measurement in the invention, no portion of the polymer was caught by the glass filter.

Next, GPC V2000, manufactured by Waters Inc., to which four columns TSKgel GMH-HT (30 cm), manufactured by Tosoh Corp., and an RI detector had been attached was used to conduct a GPC measurement. The measurement conditions used were as follows: specimen solution injection amount, 524.5 (μL); column temperature, 135° C.; solvent, o-dichlorobenzene; flow rate, 1.0 (mL/min). The molecular weights were calculated in the following manner. Commercial monodisperse polystyrenes were used as reference standards. From the polystyrene reference standards and from a viscosity formula for ethylene-based polymers, a calibration curve regarding retention time and molecular weight was drawn. Each molecular weight was calculated on the basis of the calibration curve.

As the viscosity formula, use was made of $[\eta]=K \times M\alpha$. For the polystyrenes, K=1.38E-4 and α=0.70 were used. For the ethylene-based polymers, K=4.77E-4 and α=0.70 were used.

[Synthesis Examples 1 to 3] Synthesis of Imines

Synthesis routes for synthesizing imine compound 1 and compound 2 according to the invention are shown below. In the following Synthesis Examples, the operations were performed in a purified-nitrogen atmosphere and the solvents used were ones which had been dehydrated and deoxidized, unless otherwise indicated.

[Synthesis Example 1]: (Synthesis of Ligand B-230)

Ligand B-230 was synthesized in accordance with the following scheme.

[Chem. 8]

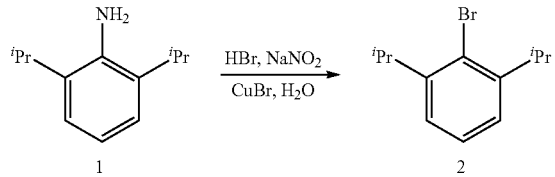

-continued

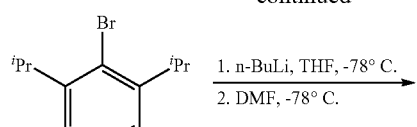

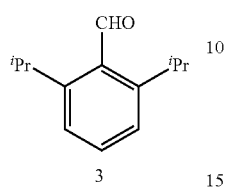

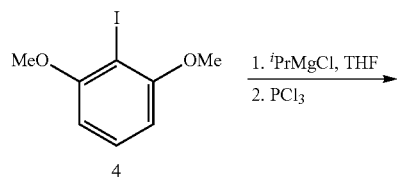

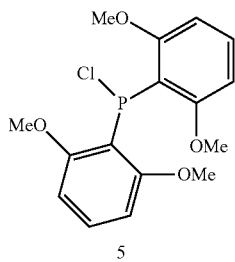

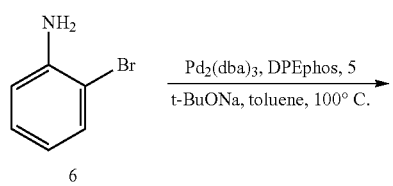

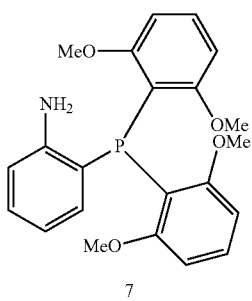

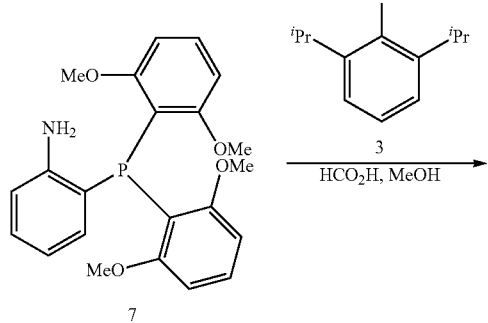

-continued

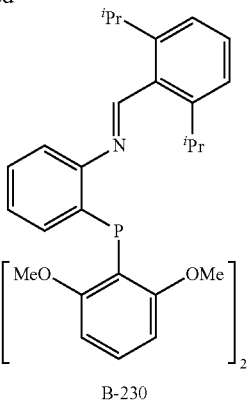

B-230

(i) A solution of sodium nitrite (6.90 g, 100 mmol) in water (100 mL) was added dropwise at −5° C. to a solution of compound 1 (17.7 g, 100 mmol) in HBr (100 mL) and water (100 mL). Furthermore, a solution of CuBr (14.4 g, 100 mmol) in HBr (100 mL) was gradually added thereto at 0° C. The reaction solution was stirred at 0° C. for 30 minutes and at 50° C. for 3 hours. After cooling to 20° C., it was treated with saturated $Na_2S_2O_3$ (200 mL), extracted with EtOAc (500 mL×3), washed with saturated $NH_4Cl_{aq}$ (200 mL), and concentrated to give crude product. The crude product was purified with a silica gel column (petroleum ether) to give compound 2.

(ii) To a solution of compound 2 (0.50 g, 2.10 mmol) in THF (10 mL) was added a hexane solution of n-butyllithium (2.5 M, 0.84 mL, 2.10 mmol) at −78° C. This mixture was stirred at −78° C. for 30 minutes and to it was added dropwise a solution of DMF (0.18 g, 6.00 mmol) in THF (3 mL) at −78° C. After the temperature was raised to 0° C., the mixture was stirred for 2 hours. The reaction was quenched by adding ice water (10 mL), and the solvent was removed under reduced pressure. The residue was extracted with EtOAc (30 mL×3), and the organic layer was washed with brine (10 mL), dried over $Na_2SO_4$, filtered, and concentrated to give crude compound 3.

(iii) To a solution of compound 4 (2.64 g, 10.0 mmol) in THF (30 mL) was added a THF solution of isopropylmagnesium chloride (2.0 M, 5.0 mL, 10.0 mmol) at −30° C. After the temperature was raised to 15° C., the mixture was stirred for 1 hour. This reaction solution was cooled to −78° C., and to this was added phosphorus trichloride (0.69 g, 5.0 mmol). The resultant mixture was stirred at −78° C. for 1 hour. The solvent was removed under reduced pressure to give compound 5.

(iv) To a solution (30 mL) of compound 6 (0.17 g, 1.00 mmol) in toluene (30 mL) were added compound 5 (0.31 g, 1.00 mmol), tris(dibenzylideneacetone)dipalladium (0.10 g, 0.100 mmol), 2,2'-bis(diphenylphosphino)diphenyl ether (0.09 g, 0.15 mmol), and sodium t-butoxide (0.19 g, 2.00 mmol) at 25° C. The mixture was refluxed for 12 hours. After cooling to room temperature, to the mixture was added ice water (30 mL). This mixture was filtered and the residue was extracted with EtOAc (100 mL×3) and the organic layer was dehydrated over $Na_2SO_4$ and concentrated. The crude product was purified with a silica gel column (petroleum ether/ethyl acetate (10/1)) to give compound 7 as a yellow solid.

(v) To a solution (100 mL) of compound 7 (5.90 g, 14.8 mmol) in methanol (100 mL) were added compound 3 (2.80 g, 14.8 mmol) and a small amount of formaldehyde at 25°

C. This mixture was refluxed for 14 hours. The solvent was removed under reduced pressure, and the residue was extracted with dichloromethane (150 mL×3). The organic layer was washed with brine (100 mL), dried over Na$_2$SO$_4$, and then concentrated. The residue was recrystallized from petroleum ether/dichloromethane (50/1) to give B-230 as a yellow solid (5.6 g, 9.8 mmol, 66% yield).

$^1$HNMR (CDCl$_3$, δ, ppm): 8.76 (s, 1H), 7.26 (t, J=7.8 Hz, 2H), 7.19-7.11 (m, 5H), 7.02 (t, J=7.4 Hz, 1H), 6.80 (t, J=6.4 Hz, 1H), 6.44 (dd, J=8.2, 2.6 Hz, 4H), 3.41 (s, 12H), 3.34-3.22 (m, 2H), 1.08 (d, J=6.8 Hz, 12H); $^{31}$PNMR (CDCl$_3$, δ, ppm) −52.6 (s).

[Synthesis Example 2]: (Synthesis of Ligand B-265)

Ligand B-265 was synthesized in accordance with the following scheme.

[Chem. 9]

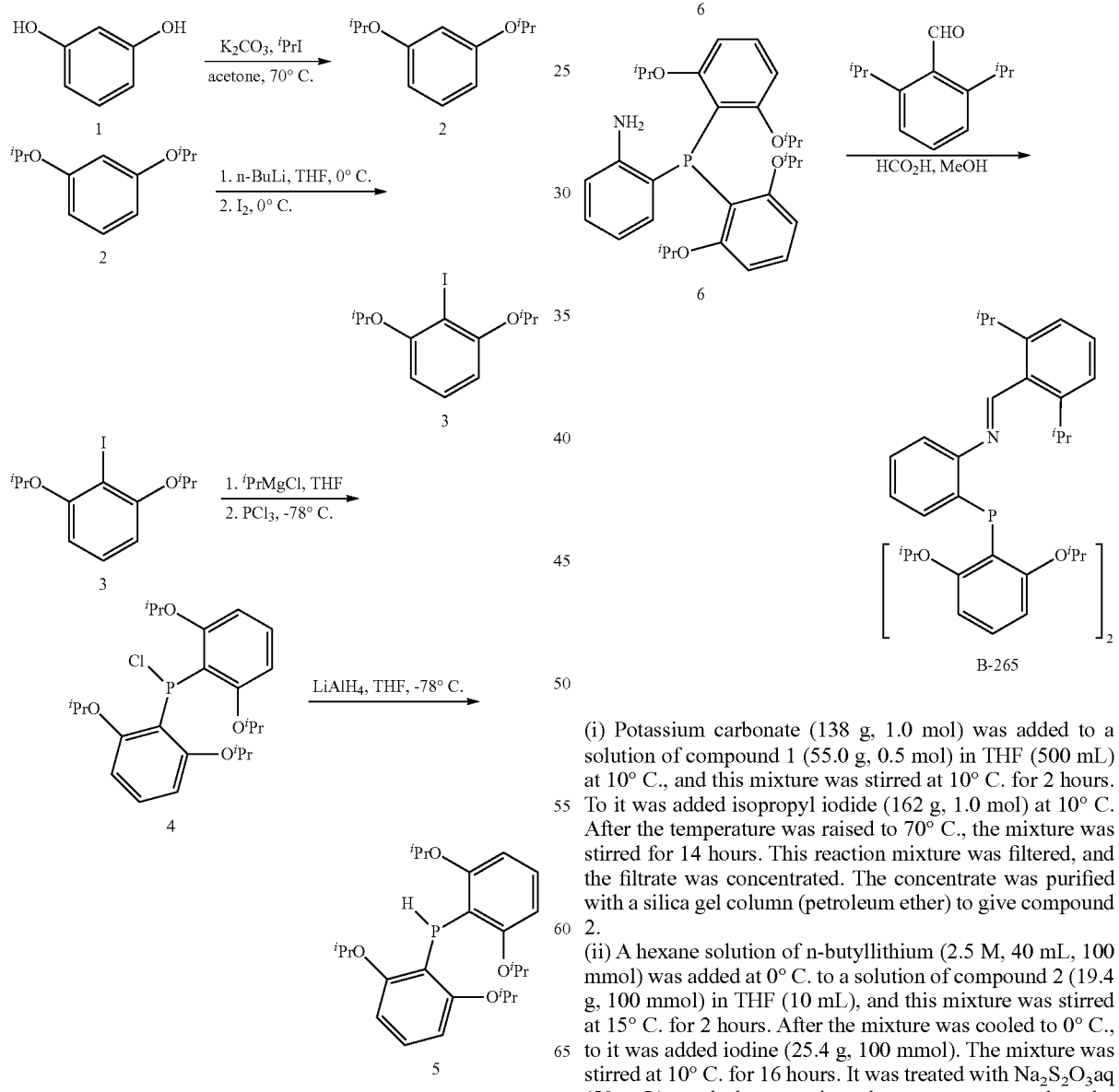

(i) Potassium carbonate (138 g, 1.0 mol) was added to a solution of compound 1 (55.0 g, 0.5 mol) in THF (500 mL) at 10° C., and this mixture was stirred at 10° C. for 2 hours. To it was added isopropyl iodide (162 g, 1.0 mol) at 10° C. After the temperature was raised to 70° C., the mixture was stirred for 14 hours. This reaction mixture was filtered, and the filtrate was concentrated. The concentrate was purified with a silica gel column (petroleum ether) to give compound 2.

(ii) A hexane solution of n-butyllithium (2.5 M, 40 mL, 100 mmol) was added at 0° C. to a solution of compound 2 (19.4 g, 100 mmol) in THF (10 mL), and this mixture was stirred at 15° C. for 2 hours. After the mixture was cooled to 0° C., to it was added iodine (25.4 g, 100 mmol). The mixture was stirred at 10° C. for 16 hours. It was treated with Na$_2$S$_2$O$_3$aq (50 mL), and the organic solvent was removed under reduced pressure. The residue was extracted with EtOAc (50 mL×3). The organic layer was dried over Na$_2$SO$_4$ and concentrated. The crude product was purified with a silica gel column (petroleum ether) to give compound 3.

(iii) A THF solution of isopropylmagnesium chloride (2.0 M, 10.0 mL, 20.0 mmol) was added to a solution of compound 3 (4.60 g, 20.0 mmol) in THF (25 mL) at −30° C. After the temperature was raised to 25° C., the mixture was stirred for 1 hour. This reaction solution was cooled to −78° C., and to it was added phosphorus trichloride (0.88 g, 10.0 mmol). The mixture was stirred at 25° C. for 1 hour to give a solution containing compound 4.

(iv) The solution containing compound 4 which had been obtained in (iii) above was added to a suspension solution of lithium aluminum hydroxide (0.38 g, 10.0 mmol) in THF (30 mL) at −78° C. After the temperature was raised to 20° C., the mixture was stirred for 16 hours. It was treated with ice water (50 mL), and the organic solvent was removed under reduced pressure. The residue was extracted with dichloromethane (100 mL×3). The organic layer was washed with brine water (100 mL), dried over Na$_2$SO$_4$, and then concentrated. The crude product was purified with a silica gel column (petroleum ether) to give compound 5.

(v) To a solution of compound 5 (1.67 g, 4.00 mmol) in toluene (30 mL) were added 2-bromoaniline (0.68 g, 4.00 mmol), tris(dibenzylideneacetone)dipalladium (0.37 g, 0.40 mmol), 2,2'-bis(diphenylphosphino)diphenyl ether (0.43 g, 0.80 mmol), and sodium t-butoxide (0.75 g, 8.00 mmol) at 15° C. The mixture was refluxed for 12 hours. After cooling to 15° C., it was treated with ice water (30 mL). This mixture was filtered and the residue was extracted with EtOAc (100 mL×3), and the organic layer was dried over Na$_2$SO$_4$ and evaporated. The residue was purified with a silica gel column (petroleum ether/ethyl acetate (10/1)) to give compound 6.

(vi) To a solution of compound 6 (1.85 g, 3.65 mmol) in methanol (20 mL) were added 2,6-diisopropylbenzaldehyde (0.70 g, 3.65 mmol) and a small amount of formaldehyde at 25° C. This mixture was refluxed for 14 hours. The solvent was removed under reduced pressure, and the residue was extracted with dichloromethane (150 mL×3). The organic layer was washed with brine (100 mL), dried with Na$_2$SO$_4$, and then concentrated. The crude product was washed with n-heptane to give B-265 (1.10 g, 1.5 mmol, 41% yield).

$^1$HMNR (CDCl$_3$, δ, ppm): 8.50 (s, 1H), 7.48-6.16 (m, 13H), 4.64 (t, J=6.0 Hz, 1H), 4.52 (t, J=5.8 Hz, 1H), 4.41-4.38 (m, 1H), 3.36-3.27 (m, 1H), 2.46-2.43 (m, 1H), 1.45-0.41 (m, 36H); $^{31}$PNMR (CDCl$_3$, δ, ppm) −48.7 (s).

[Synthesis Example 3]: (Synthesis of Ligand B-275)

Ligand B-275 was synthesized in accordance with the following scheme.

[Chem. 10]

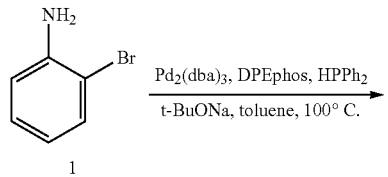

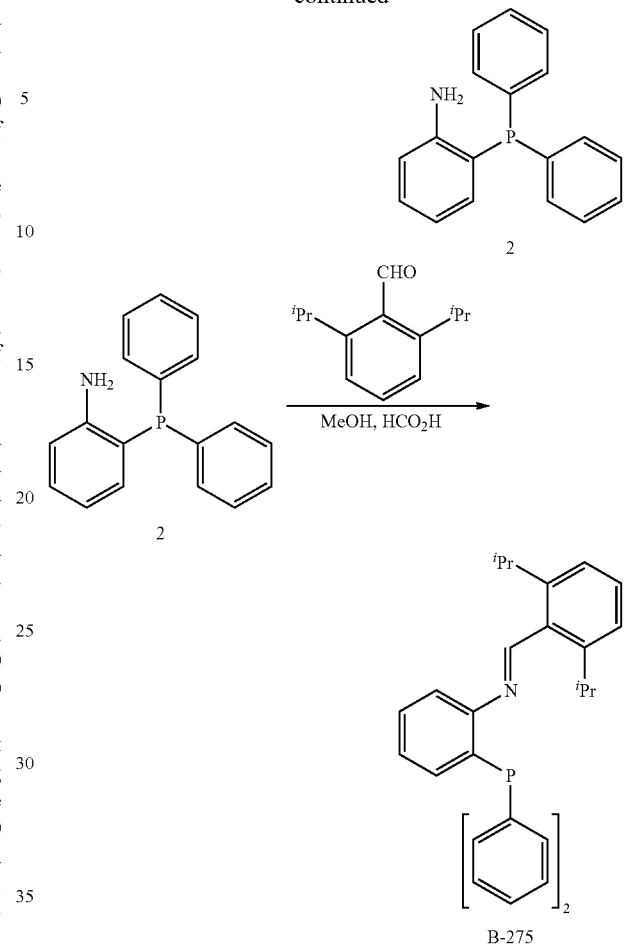

(i) Tris(dibenzylideneacetone)dipalladium (4.00 g, 4.4 mmol) was added to a solution of compound 1 (7.50 g, 43.8 mmol), diphenylphosphine (8.10 g, 43.8 mmol), 2,2'-bis(diphenylphosphino)diphenyl ether (4.70 g, 8.8 mmol), and sodium t-butoxide (8.20 g, 20.0 mmol) in toluene (200 mL). This mixture was refluxed for 12 hours. After cooling to room temperature, the mixture was treated with ice water (30 mL). This mixture was filtered, and the residue was extracted with EtOAc (100 mL×3), and the organic layer was dried over Na$_2$SO$_4$ and concentrated. The crude product was purified with a silica gel column (petroleum ether/ethyl acetate (50/1)) to give compound 2 as a white solid.

(ii) To a solution of compound 2 (1.80 g, 6.5 mmol) methanol (20 mL) were added 2,6-diisopropylbenzaldehyde (2.47 g, 13.0 mmol) and a small amount of formaldehyde at 25° C. This mixture was stirred at 80° C. for 16 hours. It was filtered to give compound B-275 as a filtration residue (1.30 g, 2.7 mmol, 43% yield).

$^1$HMNR (CDCl$_3$, δ, ppm): 8.81 (s, 1H), 7.48-6.90 (m, 17H), 3.33-3.29 (m, 2H), 1.14 (d, J=6.8 Hz, 12H); $^{31}$PNMR (CDCl$_3$, δ, ppm) −16.2 (s).

[Example 1] Propylene Polymerization Using Ligand B-230

(1) Synthesis of B-230/Nickel Complex

All of the following operations were performed in a high-purity N$_2$ atmosphere. Hereinafter, dibromo(1,2-dimethoxyethane)nickel(II) is referred to as NiBr$_2$(DME).

To NiBr$_2$(DME) (123 mg) was added a THF solution of B-230 (8 mL, 0.05 mM, 0.40 mmol, 278 mg), and the mixture was stirred for 3 hours to obtain a solution. After the filtration, the filtrate was evaporated. The residue was washed with dichloromethane and toluene to give B-230/nickel complex. This complex (79 mg) was dissolved in toluene (10 mL), and the resultant deep green complex solution was used in the subsequent polymerization operation.

(2) Propylene Polymerization

Into an induction stirring type 2 L-autoclave were introduced a co-catalyst (MMAO-3A) and propylene (500 mL). The B-230/nickel complex obtained in (1) above was introduced into the autoclave with nitrogen gas, and the autoclave was heated to a given temperature with stirring. After the given temperature was reached, the propylene was polymerized for a given time period. The unreacted monomer was purged. The autoclave was opened, and ethanol was added. The mixture was filtered, and the solid matter was dried by heating to give a polymer. The aluminum residue contained in the polymer obtained was removed by washing with a methanol solution of hydrochloric acid.

In Table 1, "Activity Vp" indicates the amount of the copolymer (kg) yielded per hour of the polymerization period per mole of the complex used in the polymerization.

[Examples 3 and 4] Propylene/Acrylic Acid Ester Copolymerization Using Ligand B-230

(1) Propylene/Acrylic Acid Ester Copolymerization

Into an induction stirring type 2 L autoclave were introduced a given amount of an acrylic acid ester as a comonomer, a co-catalyst (MMAO-3A), and propylene (500 mL). The B-230/nickel complex was introduced into the autoclave with nitrogen gas, and the autoclave was heated to a given temperature with stirring. After the given temperature was reached, the monomers were polymerized for a given time period. The unreacted gases were purged. Thereafter, the autoclave was opened, and filtration, solvent washing, and thermal drying were conducted to obtain a copolymer.

The kinds and amounts of the comonomers used in the copolymerization are shown in Table 1. The comonomers were used after having been purified at room temperature in a high-purity argon atmosphere using a column packed with Aldrich Inhibitor Remover, manufactured by Aldrich Co. The amount of toluene used for the polymerization, the polymerization temperature, and the internal pressure of the autoclave during the polymerization are also shown in Table 1.

In Table 1, MA denotes methyl acrylate, and tBA denotes t-butyl acrylate. Furthermore, "Activity Vp" indicates the amount of the copolymer (g) yielded per hour of the polymerization period per mole of the complex used in the polymerization. The results of GPC also are shown in Table 1.

TABLE 1

|  | Ligand | Amount of catalyst (mmol) | Amount of co-catalyst (mmol) | Polymerization temperature (° C.) | Comonomer | Activity Vp (kg/mol/hr) | Mw | Mw/Mn | Content of comonomer (mol %) |
|---|---|---|---|---|---|---|---|---|---|
| Example 1 | B-230 | 0.1 | 10 | 50 | none | 12.4 | 17,000 | 2.1 | — |
| Example 2 | B-265 | 0.06 | 6 | 50 | none | 9.2 | 11,000 | 2.1 | — |
| Example 3 | B-230 | 0.11 | 11 | 50 | MA 21 mmol | 8.6 | 2,500 | 1.3 | 0.05 |
| Example 4 | B-230 | 0.1 | 10 | 65 | tBA 21 mmol | 8.6 | 2,700 | 1.6 | no data |

The results of the GPC measurement on the polymer obtained are also shown in Table 1.

[Example 2] Propylene Polymerization Using Ligand B-265

(1) Formation of Complex

A complex was formed in the same manner as in Example 1, except that the B-265 (333 mg) obtained in Synthesis Example 2 was used as a ligand.

(2) Propylene Polymerization

Propylene polymerization was conducted in the same manner as in Example 1, except that the compound obtained in (1) above was used as a complex. The results are shown in Table 1.

[Comparative Example 1] Propylene Polymerization Using Ligand B-275

(I) Formation of Complex

A complex was formed in the same manner as in Example 1, except that the B-275 (219 mg) obtained in Synthesis Example 3 was used as a ligand.

(2) Propylene Polymerization

Propylene polymerization was conducted in the same manner as in Example 1, except that the compound obtained in (1) above was used as a complex. The results are shown in Table 2.

TABLE 2

|  | Ligand | Amount of catalyst (mmol) | Amount of co-catalyst (mmol) | Polymerization temperature (° C.) | Vp (kg/mol/hr) | Mw | Mw/Mn |
|---|---|---|---|---|---|---|---|
| Comparative Example 1 | B-275 | 0.13 | 13 | 50 | 23 | N.D. | N.D. |

N.D.: The molecular weight was too low to determine by GPC.

[Discussion Based on Comparison Between Results of the Examples and Results of the Comparative Example]

The polypropylenes yielded in Example 1 and Example 2 each had a molecular weight Mw exceeding 10,000, whereas the product obtained in Comparative Example 1 was an oligomer and had an exceedingly low molecular weight. It was understood that propylene products having a far higher molecular weight than polymers produced using the conventionally known catalyst are obtained by the Examples.

As demonstrated above, by using the metal complexes of the invention, polypropylene having a high molecular weight can be obtained and propylene can be copolymerized with acrylic acid esters. The rationality and meaningfulness of the constituent elements of the present invention and the superiority of the invention over prior-art techniques have become clear.

While the invention has been described in detail and with reference to specific embodiments thereof, it will be apparent to one skilled in the art that various changes and modifications can be made therein without departing from the spirit and scope thereof. This application is based on a Japanese patent application filed on Sep. 27, 2013 (Application No. 2013-201474), the contents thereof being incorporated herein by reference.

INDUSTRIAL APPLICABILITY

The metal complex, which can be easily synthesized, the catalyst including the complex, and the method for olefin polymerization according to the invention make it possible to economically produce olefin-based polymers having a molecular weight higher than that attained with conventional metal complexes, and are exceedingly useful in the industrial production of polyolefins.

The invention claimed is:
1. A compound represented by the following formula (1):

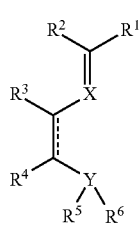

in which X represents a nitrogen atom, Y represents a phosphorus atom,
$R^5$ and $R^6$ each independently is a hydrogen atom or a hydrocarbon group which has 1-30 carbon atoms and may contain one or more heteroatoms, at least one of $R^5$ and $R^6$ being a hydrocarbon group which contains two or more heteroatom-containing groups, and
$R^1$ to $R^4$ each independently represents a hydrogen atom, a hydrocarbon group which has 1-20 carbon atoms and may contain one or more heteroatoms, or a halogen atom, and two or more groups selected from among $R^1$ to $R^4$ may be linked to each other to form an alicyclic ring, an aromatic ring, or a heterocyclic ring which contains one or more heteroatoms selected from among oxygen, nitrogen, and sulfur atoms, in which each of the rings is a 5- to 8-membered ring which may have one or more substituents thereon.

2. The compound according to claim 1, wherein $R^3$ and $R^4$ are linked to each other to form an aromatic ring.

3. A metal complex obtained by reacting a compound according to formula (1) with a complex precursor which is a compound of a transition metal belonging to Groups 8 to 10 of the periodic table, wherein the compound of formula (1) is

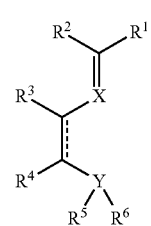

in which X represents a nitrogen atom, Y represents a phosphorus atom,
$R^5$ and $R^6$ each independently is a hydrogen atom or a hydrocarbon group which has 1-30 carbon atoms and may contain one or more heteroatoms, at least one of $R^5$ and $R^6$ being a hydrocarbon group which contains two or more heteroatom-containing groups, and
$R^1$ to $R^4$ each independently represents a hydrogen atom, a hydrocarbon group which has 1-20 carbon atoms and may contain one or more heteroatoms, or a halogen atom, and two or more groups selected from among $R^1$ to $R^4$ may be linked to each other to form an alicyclic ring, an aromatic ring, or a heterocyclic ring which contains one or more heteroatoms selected from among oxygen, nitrogen, and sulfur atoms, in which each of the rings is a 5- to 8-membered ring which may have one or more substituents thereon.

4. The metal complex according to claim 3, which is represented by the following formula (2)

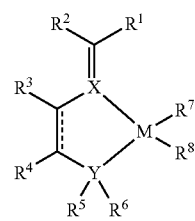

in which M represents a transition metal belonging to Groups 8 to 10 of the periodic table,
X represents a nitrogen atom, Y represents a phosphorus atom,
$R^5$ and $R^6$ each independently is a hydrogen atom or a hydrocarbon group which has 1-30 carbon atoms and may contain one or more heteroatoms, at least one of $R^5$ and $R^6$ being a hydrocarbon group which contains two or more heteroatom-containing groups, and
$R^1$ to $R^4$, $R^7$, and $R^8$ each independently represents a hydrogen atom, a hydrocarbon group which has 1-20 carbon atoms and may contain one or more heteroatoms, or a halogen atom, and two or more groups selected from among $R^1$ to $R^4$, $R^7$, and $R^8$ may be linked to each other to form an alicyclic ring, an aromatic ring, or a heterocyclic ring which contains one or more heteroatoms selected from among oxygen, nitrogen, and sulfur atoms, in which each of the rings is a 5- to 8-membered ring which may have one or more substituents thereon.

5. The metal complex according to claim 4, wherein M in formula (2) is a transition metal belonging to Group 10 of the periodic table.

6. A catalyst component for olefin polymerization which comprises the metal complex according to claim 3.

7. A catalyst for olefin polymerization which comprises the following components (A) and (B), and optionally further contains the following component (C):
   component (A): the metal complex according to claim 3,
   component (B): either a compound which reacts with component (A) to form an ion pair, or an ion-exchange phyllosilicate,
   component (C): an organoaluminum compound.

8. The catalyst for olefin polymerization according to claim 7, wherein the component (B) is an aluminoxane.

9. A process for producing an α-olefin polymer, the process comprising polymerizing or copolymerizing (a) α-olefin in the presence of the catalyst for polymerization according to claim 7.

10. A process for producing an α-olefin/polar comonomer copolymer, the process comprising copolymerizing (a) α-olefin with (b) a polar comonomer in the presence of the catalyst for polymerization according to claim 7.

11. The process for producing an α-olefin/polar comonomer copolymer according to claim 10, wherein the polar comonomer (b) is a (meth)acrylic acid ester.

* * * * *